US008765460B2

(12) United States Patent
Nordvik et al.

(10) Patent No.: US 8,765,460 B2
(45) Date of Patent: Jul. 1, 2014

(54) PHOTOBIOREACTOR SYSTEM FOR MASS PRODUCTION OF MICROORGANISMS

(76) Inventors: Atle B. Nordvik, Vienne, VA (US); George Berliner, Aliso Viejo, CA (US)

( * ) Notice: Subject to any disclaimer, the term of this patent is extended or adjusted under 35 U.S.C. 154(b) by 565 days.

(21) Appl. No.: 12/966,967

(22) Filed: Dec. 13, 2010

(65) Prior Publication Data
US 2011/0312062 A1 Dec. 22, 2011

Related U.S. Application Data

(60) Provisional application No. 61/286,359, filed on Dec. 14, 2009.

(51) Int. Cl.

| | |
|---|---|
| *C12M 1/42* | (2006.01) |
| *C12N 1/12* | (2006.01) |
| *C12M 1/00* | (2006.01) |
| *C12M 1/12* | (2006.01) |
| *C12N 13/00* | (2006.01) |

(52) U.S. Cl.

CPC ............... *C12M 21/02* (2013.01); *C12M 25/01* (2013.01); *C12N 13/00* (2013.01); *C12N 1/12* (2013.01)

USPC ..................................... 435/292.1; 435/257.1

(58) Field of Classification Search
CPC ...... C12M 21/02; C12M 25/01; C12M 31/10; C12N 13/00; C12N 1/12; C12N 1/20
USPC .......................... 47/1.4, 60; 435/257.1, 292.1
See application file for complete search history.

(56) References Cited

U.S. PATENT DOCUMENTS

| | | | | |
|---|---|---|---|---|
| 8,062,880 | B2 * | 11/2011 | Freeman | 435/257.1 |
| 2005/0135104 | A1 * | 6/2005 | Crabb et al. | 362/276 |
| 2008/0254529 | A1 * | 10/2008 | Freeman | 435/257.1 |

* cited by examiner

*Primary Examiner* — Michael Marcheschi
*Assistant Examiner* — Shanta G Doe
(74) *Attorney, Agent, or Firm* — Todd J. Langford; Eric A. Hanscom

(57) ABSTRACT

A photobioreactor system for mass production of microorganisms is disclosed. Water with microorganisms suspended therein is sprayed through a nozzle to create droplets. These droplets have a high surface area to volume ratio enabling efficient light transfer and gas diffusion. The water may also be passed through channels between two transparent plates, wherein superior mixing is achieved along with a high surface to volume ratio. The water is preferably circulated through a dark holding tank Active and passive flashing lights of different wavelengths are used to promote growth of the microorganisms when the water is sprayed and/or passing through the transparent plates.

8 Claims, 18 Drawing Sheets

50

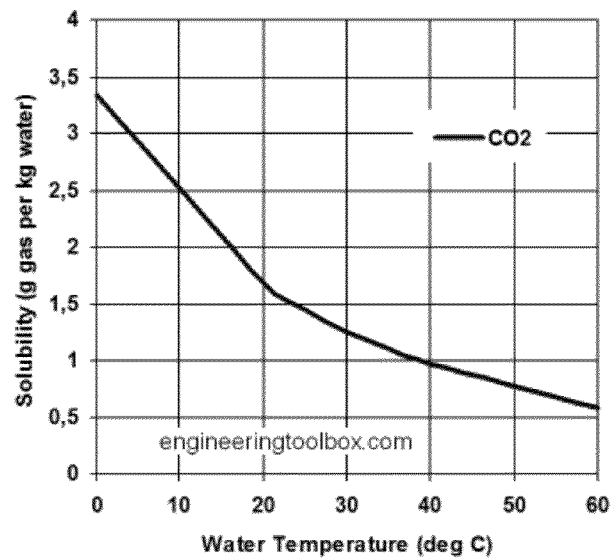
Figure 11
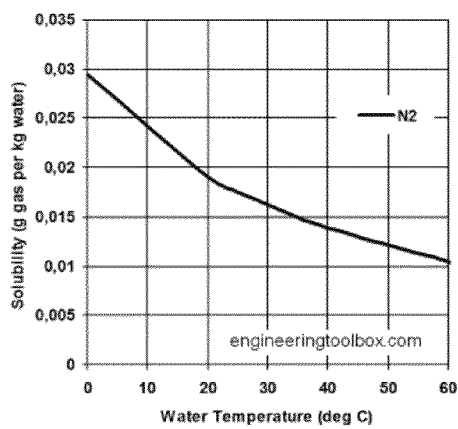　　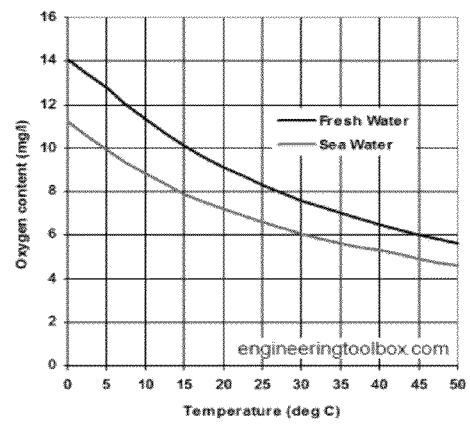
Figure 12A　　　　　　　　　　　　Figure 12B

PHOTOBIOREACTOR SYSTEM FOR MASS PRODUCTION OF MICROORGANISMS

CROSS REFERENCE TO RELATED APPLICATIONS

This application is a non-provisional of U.S. Patent Application No. 61/286,359 filed on Dec. 14, 2009.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of agricultural systems, and more specifically toward a photobioreactor system for mass production of microorganisms. The invention belongs to the category of photobioreactors (PBRs) including methods and technologies used for enhancement of biological processes for growth of microalgae and autotrophic microorganisms, especially unicellular organisms for commercial high volume production of biomass as feedstock for production of biofuel, and/or animal food, nutritious and pharmaceutical products.

The current public concern regarding climate change and emission of greenhouse gas from combustion of fossil fuels, instabilities in the fossil fuel markets, energy insecurity and increasing energy prices has accelerated the urgency for development of alternative renewable reliable energy sources and technologies.

The potential of using microalgae as a source of energy was proposed in the early 1950s using wastewater as a source of nutrients for algae production and waste water cleaning. The concept found a new life with the energy crisis of the 1970s when research focus also included use of microorganisms as an alternative and renewable energy resource. From 1978 to 1996, the U.S. Department of Energy funded a research program called the Aquatic Species Program to develop renewable transportation fuels from algae utilizing emission of carbon dioxide ($CO_2$) from coal fired power plants. More recently, the research focus has been on development of high capacity photobioreactors for production of biofuel utilizing the high lipid content in specific algae species that can be harvested, extracted and refined into transportation fuels including the fast growing and replicating eukaryotes and prokaryotes, such as diatoms, unicellular organisms and micro-algae.

Results from above mentioned and more recent research reports including studies on cell physiology, photosynthesis and biochemical reactions, chemical compositions, physical laws, environmental conditions and engineering developments has greatly affected the design, operation and development of prototype photobioreactors (PBR). Even though microalgae have been produced in bioreactors for smaller quantities for use in the nutrient and pharmaceutical industry and in research related photobioreactors for mass production of biofuel, the photobioreactor technology and biochemistry behind cell growth still needs significant research and development efforts to become a cost effective and competitive alternative source of energy according to Mobil/Exxon.

Highlights from various studies on physical and biochemical processes and technology developments that have affected the design of the prior art are included in this document as background information to simplify the understanding of processes involved in microalgae biomass production and as ease of reference in addition to issues related to the current technologies.

Design and operation of PBRs for efficient growth and mass production of biomass derived from autotrophic microorganisms are affected by fundamental genetic, biochemical and physiological processes. Important factors include cell metabolism, its functions when exposed to light and the effect of light absorbance, intensity, light saturation and photoinhabitation on photosynthesis. In addition, factors such as culture thickness and light penetration at various culture densities, diffusion rates of gases in air through the water surface and cell membranes and saturation of gases in water ($CO_2$, $N_2$ and $O_2$), changes in ph, and the influence of temperature, $CO_2$, and nutrients on photosynthetic and biochemical reactions are of importance for increasing the growth rates. Some of the most important factors are further discussed below and used as background for development of the invention in addition to problems related to current photobioreactor technologies.

Autotrophic microorganisms absorb sunlight to produce chemical energy into carbohydrates and molecular oxygen ($O_2$) from carbon dioxide ($CO_2$) and water. The energy needed to convert the light energy to chemical energy is absorbed by the pigments of chlorophylls a and b, and carotenoids. There are three broad categories of pigments that occur in algae that include (1) Chlorophylls: green, (2) Carotenoids: red, orange, yellow, amber, or brown, and (3) Phycobilins: iridescent red or blue.

All photosynthetic organisms have chlorophyll a and accessory pigments. Accessory pigments absorb energy that chlorophyll a does not absorb and include chlorophyll b (also c, d, and e in algae and protistans), xanthophylls, and carotenoids (such as beta-carotene absorbing blue light). Chlorophyll a and b absorbs its energy from the violet-blue and reddish orange-red wavelengths, and little from the intermediate (green-yellow-orange) wavelengths while carotenoids in general absorb blue to blue green and some green light.

Microalgae have the ability to adapt to different wave lengths by changing their relative amount of various pigments. This adaptation allows the algal cells to maximize light absorbance for photosynthesis. At very high light intensities, some algae produce a high concentration of "sunscreen" pigments to protect the interior of the cell from exposure to excess ultraviolet and blue light that can damage the cell. The pigments are split into two classes, xanthophylls (which contain oxygen) and carotenes (which are purely hydrocarbons, and contain no oxygen).

The types of pigments vary among different species and only a limited number of wavelengths in the visible spectrum are absorbed by the cells to regulate specific cell functions. Red light at 650 nm stimulates growth and cell development and can increase the growth of some plants up to ten times the normal rate. When red light at 700 nm is in conjunction with 650 nm red light, photosynthetic activity is considerably greater than with either single frequency.

Blue light at 420 nm enhances the effect of 650 nm red light and regulate phototropism, the movement toward light for photosynthesis, the stoma openings in cell membranes for water and gas exchange of $CO_2$, and the chlorophyll synthesis known as the process where enzymes produces chlorophyll unlimited in first 6-12 hours of light. The last step of chlorophyll synthesis requires high levels of blue light. The other blue light responses are triggered by lower levels of blue light. Cells grown in blue light will photosynthesize almost four times as fast as cells grown over red light.

The action spectrum of photosynthesis is the relative effectiveness of different wavelengths of light at generating electrons from photons in light. The absorption occurs mostly in the blue and red spectrum. The optimum rates of photosynthesis for chlorophyll a and b and Carotenoid pigments are at wavelengths at about 450, 680 and 700 nanometers (nm) for blue and red respectively. FIG. 1 illustrates the action spectrum of wavelengths in nanometers for light being absorption by pigments.

The ratio of chlorophyll to carotenoid determines the color of the microorganism and they usually produce more chlorophyll in darker periods, thereby masking the orange, red, or yellow carotenoid colors.

Light behaves like a stream of particles (quanta) called photons and the different wavelengths of light have photons of different energy levels. Short wavelength photons (blue light) have a higher energy than long wavelength (red light) photons. FIG. 2 illustrate the wavelengths for x rays, UV, visible light and infrared radiation.

Chlorophyll absorbs the light as individual photons and each photon can cause a single photochemical reaction. If there is no direct photochemical reaction, chlorophyll may lose its excitation energy as heat and red-fluorescence, or by resonance transfer. When a pigment molecule absorbs a photon, it raises its electrons to higher energy levels. The pigment is excited and can perform photochemical reactions. This excitation energy is used in photochemical reactions. The energy (E) in a photon is determined by the wavelength ($\lambda$) of the light according to the following equation:

$$E = \frac{hc}{\lambda}$$

Where h is Planck's constant, or $6.6\times10^{-34}$ J s, and c is the speed of light, or $3\times10^{8}$ m s$^{-1}$.

There is however a limitation in how much energy a cell can process and too much energy reduces the photosynthetic efficiency and cell growth. Each cell should therefore not receive more photons than it can convert into chemical energy. However, it is impossible to control the energy level to each cell in an aquatic culture or the duration of irradiation in photobioreactors because only the cells closest to the surface receive the incident photon energy. The cells further away will receive lower intensity light or no light at all, because of shading from other cells and that the intensity of a light beam decreases rapidly (approximately exponentially) as it transverses the culture.

The pigments are located in membranous sacs in the chloroplast. If a pigment absorbs light energy, one of three things will occur, (1) the energy is dissipated as heat, (2) the energy may be emitted immediately as a longer wavelength, a phenomenon known as fluorescence, or (3) the energy may trigger a chemical reaction, as in photosynthesis. Chlorophyll only triggers a chemical reaction when it is associated with proteins embedded in a membrane such as in a chloroplast in a eukaryote cell or in the membrane sacs in prokaryote cells such as cyanobacteria and prochlorobacteria. FIG. 3 illustrates an algal eukaryote cell showing the cell structure and the location of chloroplast.

Chloroplast has a complex membrane system consisting of an outer (host) membrane and an inner (bacterial) membrane. Inside the inner membrane in the region called the stroma, is a system of interconnecting lamella (flattened) membrane compartments. They may occur singly and called intergrana, or they may be stacked like coins and called grana, or they may exist as individual "coins" called thylakoids. The lumen of the lamellae contains the oxygen generating system and the stroma region around the interconnecting lamellae contains the $CO_2$ fixing system. FIG. 4 illustrates the structure of chloroplast and its membrane structure.

The light absorbing pigments in the thylakoid membranes transfer energy to reaction centers called photosystems. The photosystems are located inside chloroplasts and secured within the thylakoid membrane with exposure to the thylakoid lumen on one side and to the chloroplast stroma on the other side. Two families of photosystems exist including Photosystem I (P700) in chloroplasts and in green-sulphur bacteria, and Photosystem II (P680) in chloroplasts and in non-sulphur purple bacteria. Photosystem I (PSI) use chlorophyll a, in the form referred to as P700 whilst Photosystem II (PSII) uses a form of chlorophyll a known as P680. The numbers 700 and 680 refers to the wavelength of light in nanometers where the pigments are most reactive.

In PSI the chlorophyll a absorbs one photon and releases one electron. The electrons are transported via the electron transport chain to PSII where reduction takes place and nicotinamide adenine dinucleotide phosphate (NADPH2) is generated. Via photolysis of water into oxygen and protons, the electron is regenerated at the chlorophyll. As a result, a proton gradient across the thylakoid membrane is created and this gradient is used by adenosine diphosphate (ADP) synthase to generate adenosine tri-phosphate (ATP).

PSI and PSII are working together to form a unique photosynthetic chain able to extract electrons from water, creating oxygen as a byproduct. PSII is the first protein complex in the Light-dependent reactions. The enzyme uses photons of light to energize electrons which are then transferred through a variety of coenzymes and cofactors to reduce plastoquinone to plastoquinol. The energized electrons are replaced by oxidizing water to form hydrogen ions and molecular oxygen. By obtaining these electrons from water, PSII provides the electrons for all of photosynthesis to occur. The hydrogen ions (protons) generated by the oxidation of water help to create a proton gradient that is used by ADP synthase to generate adenosine tri-phosphate (ATP). The energized electrons transferred to plastoquinone are ultimately used to reduce NADP+ to NADPH or are used in Cyclic Photophosphorylation. FIG. 5 illustrates the Light-dependent reactions of photosynthesis at the thylakoid membrane.

The photosynthesis process takes place in two distinct stages with the first being the light-dependent reactions that require light to function and the second being the light-independent reaction, often referred to as the dark reaction because it does not require light.

In the light dependent reactions, the energy of light is used to "split water," stripping a pair of electrons from it (and causing the two hydrogens to be lost), thus generating molecular oxygen. The energy in light is transferred to these electrons, and is then used to generate ATP and the electron carrier NADPH. These two products carry the energy and electrons generated in the light reactions to the stroma, where they are used by the dark reactions to synthesize sugars/carbohydrates from $CO_2$.

In the light-independent reactions, $CO_2$ from the atmosphere (or water for aquatic/marine organisms) enters single-celled and aquatic autotrophs by diffusion and is then modified by the addition of hydrogen to form carbohydrates (general formula $[CH_2O]n$. In the reaction, enzymes starting with Ribulose-biphosphate carboxylase (Rubisco) use ATP and NADPH to synthesize 3-carbon-sugars (C3-sugars) from carbon dioxide. Then, C3-sugars are combined to form molecules of glucose. Glucose can be converted to polysaccharides which serve as building materials or to fatty acids which serve as building blocks for membrane lipids or as a source of energy storage.

The enzymes in the dark reaction are temperature dependent and therefore predominantly define the optimal temperature in which the species can grow. The light-dependent and dark reactions in the two-stage photosynthesis processes are illustrated in FIG. 6.

The time scale of photosynthetic processes can range from picoseconds to minutes and can be divided into three ranges according to the time period a process takes place: (1) the primary photochemistry process takes within picoseconds ($1 \times 10^{-12}$ of a second) to nanosecond ($1 \times 10^{-9}$ of a second), (2) electron transport process takes within microsecond ($1 \times 10^{-6}$ of a second) to millisecond ($1 \times 10^{-3}$ of a second), and (3) carbon metabolism process takes within second to minutes.

Even though light is crucial for photosynthesis, long duration of cell exposure to light (photoperiod), high light intensity, (sun or artificial) can limit the growth of microorganisms and the most important factor limiting the yield per unit area of exposed surface lies in the characteristic of light saturation.

Depending on the marine species of microorganisms, the cells only needs light intensity from about 200 to 400 µE/m2/s to achieve optimum growth and that is significantly lower than tropical sunlight intensity of about 2000 µE/m2/s. An increase of light intensity (irradiance) increases the growth rate, but only until the light saturation point is reached for the specific organism and well before full sunlight intensity is reached. This is caused by the fact that algae are able to absorb far more photons than they can collect and transfer into PS-I. Above this threshold, increasing the irradiance level alone produces no increase in the rate of photosynthesis or positive effective growth rate. The light-dependent reactions are therefore producing more ATP and NADPH than can be used by the light-independent reactions in PS-I for $CO_2$ fixation. A further increase in the cell's rate of photosynthesis at the point of saturation may require access to additional $CO_2$.

FIG. 7 illustrates the light saturation point at an increasing level of irradiance where the rate of photosynthesis reaches its maximum value.

An increase of irradiation (intensity) above the light saturation point causes reduction of the growth rate and can potential damage or kill algae, because it overloads their photosystems. This can even bleach out their pigments and/or cause reduction of the light absorbing chlorophyll in PSII, creating a region of irradiance referred to as photoinhibitation.

The photoinhibited PSII centers are continuously repaired via degradation and synthesis of a protein of the photosynthetic reaction center of PSII [9]. However, if the light intensity is too high, a permanent damage to the light absorbing pigments may occur. When high light can lead to photoinhibition, high oxygen concentrations in the culture medium from cell respiration can lead to photooxidation and reduced growth of cells in open ponds and closed PRB's. The reduction in specific growth rate in the photoinhibited region is illustrated in FIG. 8.

Growth limitation as a result of light saturation and photoinhabitation can be minimized by use of high intensity flashing light in combination with higher concentrations of $CO_2$ and nutrients. As a result, flashing light enhances micro-algal biomass productivity and overall photosynthetic efficiency. Laboratory testing on photosynthesis in intermittent light started already in 1905 when a rotating disk with a cut-out section to chop the light from a lamp was used to create flashing. It was demonstrated that 75% of the light from a given source could be blocked without decreasing the rate of photosynthesis and that the yield (the weight of algae grown per unit time) could be increased. The improvement in the yield, of the intermittent light over the yield in continuous light was found to be depended on the frequency of the flashing and that the light period needed to be followed by sufficiently long dark periods. The frequency of 0.07 Hz resulted in a 10% improvement in yield and at 133 Hz the improvement was 100%. An improvement of 400% was achieved when only 50 Hz was used. In this case the light flashes were made much shorter than the dark periods with only 17% light duration (the duration of one light cycle at 50 Hz is 0.02 second and 17% light duration equals 0.0034 second, and the corresponding dark period is 0.0166 second). FIG. 9 shows the photosynthesis per unit light as a function of the time the light was on.

The data from FIG. 8 illustrate that a given amount of light at 95% illumination (blue arrows) gives 4.4 units of photosynthesis, and when the light is on only 17% of the time (red arrows), the same amount of light gives 17.7 units of photosynthesis. Experiments have also indicated that the light reaction begins at about 0.001 second per flash and is dependent on the concentration of carbon dioxide and temperature.

The productivity of microalgae cultures is determined by a number of factors including: (1) physical factors such as light (quality, quantity and duration), temperature, nutrients, $O_2$ and $CO_2$; (2) biotic factors including pathogens, predation and competition by other algae; and (3) operational factors such as: shear produced by mixing, dilution rate, harvest frequency and culture thickness. Among these, light is undoubtedly the key parameter in designing a successful PBR. The two properties of light energy of greatest importance for algal growth and metabolism are the wavelengths absorbed by the pigments and intensity. Studies have shown that productivity and growth rate increases significantly when the culture thickness decreases such as by reducing the depth in ponds, the diameter of tubular reactors and the distance between the walls on flat plate photobioreactors. A reduction of culture thickness from 6.0 cm to 0.7 cm resulted in an increase in productivity from 2.9 ml/l/d to 23.0 ml/l/d with the largest increase was measured from 2.0 cm to 0.7 cm.

Loss of photon energy in the water column results in significant reduction in the photon energy. The loss is caused by shading of cells in high density cultures and scattering such as reflection, refraction and diffraction in addition to light absorbance by the cells. The dramatic decrease in light intensity penetrating high density cell cultures, the light penetration depth will be shorter than 1.0 cm at a cell concentration of as low as 1 g/L, and studies have indicated that more than 90% of 680 and 440 nm light (red and blue colors) will be absorbed by the cells within 1.0 cm of the illumination at the surface. This mutual shading will decrease the portion of the cells exposed to the light and only the cells close to the illuminated surface are exposed to meaningful light levels at high cell densities regardless of the supplied light intensity.

The productivity is also greatly affected by delivery and the distribution of the light, the light scattering and the reduction in photon energy in the culture, in addition to variations in diurnal changes in irradiance due to cloudiness, solar angel and seasonal variations of photon flux density. Management of operational factors may compensate some for the changes in sunlight so that the cells are exposed to their optimum average photon flux density, by optimization of pond depth, cell density, turbulence and the dilution cycle (reduction of cell density) and harvesting frequency, all of which affect the amount of light received by the cells.

Each cell needs a minimum level of photon energy and $CO_2$ to execute photosynthesis, and this level increases when the number of cells increases as a result of cell splitting. The increased cell concentration from cell splitting and size increase result in higher density and mutual blocking of light that reduces the energy level below what is required to initiate photochemical reactions in PSII. The photon energy needs to be large enough to break up a water molecule into hydrogen and oxygen for the hydrogen to combine with $CO_2$ to make carbohydrate hydrocarbons/sugar as part of the photosynthesis reactions. This threshold/activation energy level has been reported to be approximately 13,000 cal. per mole when tested on isolated chlorophyll. Lower energy photons are insufficient regardless of how many photons there are (i.e. how bright the light is). Below a certain level of photon flux density, carbon uptake is negative, as respiration exceeds photosynthesis. As irradiance increases, a compensation point is eventually reached where $CO_2$ through photosynthesis is exactly balanced by losses through respiration. Above the light compensation point, uptake increases linearly until the amount of carboxylation enzyme or available $CO_2$ limits the process.

Measurement of oxygen production from the cells is a direct indication of the photosynthesis reactions and is used to determine the photosynthetic efficiency, saturation point, $CO_2$ consumption, and penetration depths at various culture densities and thicknesses. The photosynthetic efficiency is a function of the wavelength of the photons, and red light has lower energy per photon than blue light. The theoretical photosynthetic yield for red light (680 nm) and for blue light (480 nm) is 33.3% and 23.5%, respectively. The theoretical photon energy required for a high density culture to initiate and undergo photosynthesis at their maximum rate has been studied. If all the photons are provided at 680 nm, approximately 30 mW/mL is required to initiate photosynthetic reactions and the energy level to reach maximum productivity was in the range of 80 mW/mL. FIG. 10 illustrates typical growth curves from the two different flat plate laboratory PBRs used during the tests. PBR-1 and PRB-2 had a culture thickness of 1.0 and 1.55 cm respectively. The growth curves are shown as solid circle and square dotted lines and corresponding oxygen production rates are the dotted lines with the thickest dots representing the PBR-1.

The minimum photon (light) energy required to initiate the growth of a specific cell was 17 pW/cell (pW stands for pico watt). The approximate saturation point was calculated to be about 160 pW/cell, and the most economic operating point (measured as oxygen production) from was determined to be at $2 \times 10^7$ cells/mL with 3.5 mW/cm$^2$ of light.

Irradiation of a single algal cell such that the incident intensity seen by the cell is near the point where the curve of photosynthetic rate vs. intensity begins to flatten out (ref. the saturation point in FIG. 7), is considered optimum. However, under practical conditions in full scale PBRs it is impossible to provide optimal illumination for every cell in the culture, and the major limiting factor in high-density algal cultures is light delivery, resulting from mutual shading of cells. Dilution of dens cultures to a level where mutual shading does not occur is a common method used to maintain a given productivity in ponds by providing higher average photon energy to each cell.

Gas transfer is the movement of gases from higher concentration to lower concentrations and is an important issue in PBR design. Carbon dioxide has to be supplied and dissolved into the culture broth and oxygen produced by the cells has to be removed. Substances, such as water, ions, and molecules needed for cellular processes, can enter and leave cells by a passive process such as diffusion. Diffusion is random movement of molecules but has a net direction toward regions of lower concentration in order to reach equilibrium. Simple passive diffusion occurs when small molecules pass through the lipid bilayer of a cell membrane. The rate of diffusion is different for various types of membranes including the water surface layer and the different cell membranes. Facilitated diffusion depends on the carrier proteins imbedded in the membrane to allow specific substances to pass through that might not be able to diffuse through the cell membrane. The rate of diffusion is affected by properties of the cell, the diffusing molecule, and the surrounding solution.

Carbon dioxide may double the rate of photosynthesis and growth of algae if the percentage of carbon dioxide made available for cell growth is doubled. Aquatic microorganisms such as algae get $CO_2$ from the air by diffusion and more $CO_2$ is needed during the light-independent reaction when light intensity is increased. The rate of photosynthesis under normal environmental conditions is the limiting factor at the point of light saturation. Carbon dioxide is abundantly present in the atmosphere, but its concentration of about 350 ppm (0.035%) must be increased several-fold before it can be used in the forced feeding of algae to avoid $CO_2$ starvation. A minimum of two pounds of carbon dioxide and one-twelfth pound of combined nitrogen are required, for every pound of dry algae harvested.

Cell membranes are using hydrophobic and oelophilic substances to enhance intake of $CO_2$ by removing boundary layer resistance to $CO_2$ diffusion (membrane built up of silicone are hydrophobic). Cell membranes can also be biochemically treated to increase the diffusion and reaction rates of photosynthesis. In addition to photo reactivity, biocatalytic coatings and biocatalytic membranes can also concentrate microorganisms at a phase boundary between a gas and a liquid.

When $CO_2$ is dissolved in water through diffusion, it reacts with water and forms carbonic acid ($H_2CO_3$) until $CO_2$ reaches an equilibrium with carbonic acid ($CO_2 + H_2O = H_2CO_3$). Diffusion of $CO_2$ into water is a slow process and less than 1% of the $CO_2$ dissolved reacts with water and forms carbonic acid and the majority of $CO_2$ stays as $CO_2$ molecules. The rate of dissolution depends on the:

Surface area of the membrane
The difference in concentration between two solutions
Nature of the solvent and solute (water and $CO_2$)
Permeability of the membrane
Molecular weight of a substance
Distance through which diffusion takes place—the greater the distance to diffuse the slower the rate of diffusion.

The amount of $CO_2$ that can be dissolved in the water decreases with increasing temperature and may lead to $CO_2$ starvation. The factors in shortest supply of $CO_2$, light, and nutrients may become the limiting growth factor and all needs to be in sufficient quantities to obtain optimum sustained productivity. The reduction in solubility of $CO_2$ in water at increasing temperatures is as shown in FIG. 11.

Nitrogen ($N_2$) and oxygen is also needed for cell growth and nitrogen increases the cell's lipid content [40]. $N_2$ has low solubility in water, and it diffuses out of an air bubble more slowly than oxygen diffuses from the water into the air bubble and the differential partial pressures drive oxygen from the water into the bubble. Solubility of oxygen and nitrogen in water at one atmosphere and different temperatures are indicated in FIG. 12.

Dissolved Oxygen (DO) produced by the cell during the photosynthetic activity is known to act as an inhibitor to photosynthesis. Open ponds and photobioreactor systems are therefore equipped with degasser devices/zones that removes DO. A common method used to remove DO is by aeration. FIG. 13 illustrates the evolution of oxygen ($O_2$) by algae per square meter per hour as a function of photosynthetic active radiation (PAR) of super thin cultures (6-8 mm).

Mixing of the fluid is important for achieving high cell concentration in a PBR and to keep the cells in suspension, eliminate thermal stratification, help nutrient distribution, and improve gas exchange. Furthermore, mixing can reduce the degree of mutual shading and lower the probability of photoinhibition. Proper mixing in the direction perpendicular to flow will significantly reduce the mutual shading and thus increase the portion of the cells exposed to the light. This mixing will also move the cells close to the illuminated surface into the center of the PBR, which will give these photon saturated cells the opportunity to use up all the absorbed light energy for photosynthesis before they are exposed to the light again. As a result, a proper mixing may significantly improve overall light utilization efficiency.

Sparging or bubbling is also a method to improve overall light utilization efficiency in two ways: (1) existence of air bubbles will increase light penetration depth, and (2) rising motion of bubbles will induce some degree of mixing tangential to the flow direction. Sparging is however a method to increase gas exchange rates and includes transfer of air ($CO_2$ and nitrogen) and removal of dissolved oxygen. In small ponds and photobioreactors this is done simply by laying a bubble diffuser tube in the bottom of the pond. Larger systems that require higher $CO_2$ concentrations use pure $CO_2$ or $CO_2$ enriched air from $CO_2$ diffusers. The $CO_2$ enriched air may contain from 800 ppm to 5000 ppm (0.8%-5%) $CO_2$. The effectiveness of aeration is dependent on the bubble size and bubble surface area, rise velocity, distribution and bubble density. Too high density results in coalescence of bubbles that reduces the total air bubble surface area and the effectiveness of mass transfer. In addition, the bubbles reduce the light penetration and slow down the growth.

Mixing and sparging methods used to bring more $CO_2$-depleted water in contact with air so that atmospheric $CO_2$ will diffuse into the water include stirring and use of $CO_2$ diffusers to bubble $CO_2$ through the water or a combination of both. An increased air-water surface area will help achieve equilibrium of $CO_2$ in water with the $CO_2$ level in the atmosphere. The dissolved $CO_2$ level affects the pH level and an increasing temperature reduces the level of $CO_2$ dissolved in the water. Mixing/stirring methods of the algae suspension includes paddle wheels in ponds, and pumps and propellers in tubular and airlift systems. In summary, mixing is being used to:

- Create flashing effects
- Transfer cells to the illuminated surface to optimize light absorption
- Remove gaseous products (excess gases such as $O_2$)
- Facilitate uniform distribution of nutrients and heat
- Improve gas exchange between the culture medium and the air ($CO_2$+N)
- Keep cells in homogeneous suspension and prevent sedimentation The above mentioned bullet items are also considered key factors for optimal bioreactor design and is an issue with many current photobioreactor technologies and designs One of the most significant challenges to achieve cost effective and efficient low cost production of biomass is how to provide each cell with the accurate amount of photon energy needed in the growth phases from incubation to harvesting. In this period the culture goes through several growth phases where the number of cells, cell dimension, and the cell concentration increases rapidly. Cultivation can be conducted in batch, semi-batch, and continuous systems. For a culture growing without limitation by carbon dioxide or nutrient and at constant temperature and constant high light intensity, a growth curve similar to the solid line ABDEF in FIG. 14 as been observed experimentally for *Chlorella* green algae, where N represents cell numbers. At low cellular densities, growth at first proceeds exponentially along the curve AB, then along a linear segment DE, and finally along a region of decreasing slope EF (the dotted line is from an unpublished test with extremely high temperatures).

The cell concentration and size of the algae during the growth period is illustrated in FIG. 15. The two growth curves marked with ○ and ● corresponds to the average cell sizes marked □ and ■ respectively and refers to two different light intensities. Closed symbols are for a low intensity and open markers for high intensity light.

Harvesting includes separation, oil extraction and drying processes. Harvesting of low density cultures needs to go through several processes to reduce water content and the separated water containing valuable nutrients needs to go back into the reactor. Cost of separation is estimated to represent 20 to 30% of operational costs for low density systems such as raceway ponds and decreases with increasing densities. Low density cultures are 0.5 g/l and extremely high densities are about 55 g/l dry weight. The separation method used is dependent on the algae species and the end product. The most common commercial method is centrifugation by use of standard separators. Other methods include separation by chemical flocculation using alum and ferric chloride, microfiltration, and natural settling. Algae oils have a variety of commercial and industrial uses, and are extracted through a wide variety of scientific methods that may include:

- Extraction by use of chemical solvents
- Soxhlet extraction is an extraction method that uses chemical solvents.
- Enzymatic extraction (uses enzymes to degrade the cell walls)
- Expression/Expeller press (when algae is dried it retains its oil content, which then can be "pressed" out with an oil press)
- Osmotic shock (sudden reduction in osmotic pressure cause cells to rupture)
- Supercritical fluid ($CO_2$ is liquefied under pressure and heated to the point that it has the properties of both a liquid and a gas)
- Ultrasonic-assisted extraction (creates cavitation bubbles in a solvent material that causes those cells walls to break and release their contents)

The two major bioreactor categories current in use include the open ponds and the closed photobioreactors. Over 98% of commercial algae biomass production is currently produced with open ponds, even for high value nutritional products. The open ponds include raceway, circular and rectangular designs while the closed designs include horizontal and vertical tubular reactors, vertical and tilted flat plate, and bubble column and air lift photobioreactors.

A raceway pond is made of a closed loop recirculation channel that is typically about 0.3 m deep. Open pond has moderate surface-to-volume ratio of 3-10/m. Cooling is mostly done by evaporation, and the pond is illuminated solely by sunlight. Paddlewheels are used to circulate the suspended algae throughout the raceway channels and to prevent sedimentation of microalgae at the bottom. The paddle wheel also mixes air into the water and creates turbulence when feeding the culture. In addition they are equipped with bubbler systems for adding $CO_2$. Flow is guided around bends by baffles placed in the flow channel. During daylight the culture is fed continuously in front of the paddlewheel where the flow begins. Broth is harvested behind the paddlewheel, on completion of the circulation loop. FIG. 16 shows areal view of the design of raceway ponds operated by paddle wheels with flow direction, baffles and positions for feeding and harvesting.

The raceway pond can be operated continuously with growth medium and carbon dioxide feed continuously added to the pond while algal broth is harvested at the end of the circulation loop. Due to reduced light penetration in the water column, ponds have low productivity and typically yield only 0.1-0.2 g/L algae. Production in the pond usually takes 6-8 weeks to mature. Open ponds are dependent on weather because temperature and light intensity vary throughout the day and year. Low temperatures (less than 17° C.) reduce algal growth rate while high temperatures (greater than 27° C.) may kill algal cells. Open ponds are cheap to build and fairly easy to clean but have several technical and operational disadvantages.

The limitation with raceway pond includes high evaporative losses, diffusion of carbon dioxide to the atmosphere, contamination risk, poor mixing and mass transfer rate, temperature fluctuation, the inability to sustain an optically dark zone to effectively prevent saturation and photoinhabitation, and requirement of large land area. The biomass productivity remains low and the algal strain of interest is difficult to cultivate. The highest operating cost for an open system is the harvesting cost since the biomass concentration is usually low and the volume is up to several hundred tons for each system. FIG. 17 shows drop in light intensity from top to bottom in an open pond and productivity at various depths at high light intensity resulting in reduced growth and lower productivity.

Closed photobioreactor include the flat plate, tubular and vertical column designs. Their design has been driven by a need for improvement of biomass production, smaller footprint, reduction of environmental contamination, improvement of light efficiency, and reduction of production costs. The systems have higher efficiency and cell concentration (2-5 g/L), better gas transfer, shorter harvest time (2-4 weeks), and higher surface-to-volume ratio (25-125/m) than open ponds. They provide better control of cultivation conditions, yield higher productivity and reproducibility, reduce contamination risk, and allow greater selection of algal species used for cultivation. Light source is usually a combination of natural light and artificial lighting. Light can be radiated inside the bioreactor with optical fibers or submerged lamps, or provided externally by the sun or by fluorescent lights). Only the tubular design is in commercial operation.

Closed systems are more expensive than ponds, and present major design and operating challenges (overheating, fouling, gas exchange limitations, etc.). Most importantly, they cannot be scaled-up for individual growth units beyond about a thousand square feet (~100 m$^2$), often much less. Biofuel production will require systems of hundreds of acres which mean tens of thousands of closed units, at high capital and even greater operating costs. Challenges with closed photobioreactors include regulation of carbon dioxide and dissolved oxygen levels, reduced light penetration into the center of reactor creating dark zones, cell growth on the walls, scale-up, and cost.

The scale-up of bioreactors increases the percentage of dark zone and reduces algal growth. The highest cost for closed system is the energy cost associated with the mixing mechanism. Tubular photobioreactors have a large surface-to-volume ratio, occupy small ground space, and require simple temperature control methods. A small scale bioreactor can be easily incorporated into a pilot plant as an indoor or outdoor system Tubular photobioreactors consist of transparent tubes that are made of flexible plastic or glass. Tubes can be arranged vertically, horizontally, inclined, helical, or in a horizontal thin-panel design. Tubes are generally placed in parallel to each other or flat above the ground to maximize the illumination surface-to-volume ratio of the reactor. The diameter of tubes is usually small and limited (0.2 m diameter or less) to allow light penetration to the center of the tube where the light coefficient and linear growth rate of culture decrease with increasing unit diameter. Growth medium circulates from a reservoir to the reactor and back to the reservoir. A turbulent flow is maintained in the reactor to ensure distribution of nutrients, improve gas exchange, minimize cell sedimentation, and circulate biomass for equal illumination between the light and dark zones.

Tubular photobioreactors consist of the optical and gas exchange units. The optical unit consists of many tubes of about 3-10 cm in optical path (distance the light has to travel across i.e. the tube diameter) and 25-80 meter long transparent tubes operated at biomass concentrations of 1 to 5 grams per liter dry weight. The transparent light-harvesting tubes are often in small diameters to provide a high surface area-to-volume ratio and photosynthetic activity. The second unit containing the fresh culture medium is the gas exchange component where exhaust gas is ventilated, air/$CO_2$ is supplied and the culture cooled. The culture is circulated between those two units by a pump and biomass is harvested by pumping the culture directly to a separate harvesting unit.

A typical horizontal tubular system design is illustrated in FIG. 18 with a picture showing an 80 meter long horizontal tubular photobioreactor.

Tubular photobioreactors do not work well in large scale production because the surface-to-volume ratio is lower causing poor light absorption. Length of tubes is another concern of tubular photobioreactors. As the length of the tubes gets larger, the time for microalgae exposure to light increases, hence increasing the absorption of available carbon dioxide and increasing photosynthesis rate. However, the dissolved oxygen level also increases which can easily lead to oxygen poisoning, and photoinhibition can result from the excess light exposure. In addition, the increasing tube length could increase liquid friction inside the tube and the head pressure of the pump, requiring a larger pump and more power consumption. If the system is built with manifolds, it would reduce the size of the pump needed and extend the path length the microalgae would take, therefore lowering the dissolved oxygen concentration and reducing the potential of cell damage.

Among the major disadvantages with tubular photobioreactors are limitation in light penetration and distribution, and pipe fluid dynamics. The shape and diameter of the tubes and thickness of culture create light and dark zones and lack of mixing result in inefficient gas mass transfers that can lead to inhomogeneous conditions and too high dissolved oxygen levels, resulting in limited growth. A continuous exposure of sunlight may also result in light saturation and inhabitation. FIG. 19 illustrates the light and dark zone by showing irradiance profiles inside a 0.06 m diameter transparent tube and a specific helical coil tubular design including a circular coil of transparent houses for irradiance.

Vertical tubular reactors (VTR) include the airlift and bubble column reactors that use airlift pumps to create circulation and turbulence. The reactors are normally composed of polyethylene or glass tubes to allow good light penetration.

Air is bubbled at the bottom to provide good overall mixing, sufficient supply of $CO_2$, and efficient removal of $O_2$. VCR) Air-lift bioreactors are similar to bubble column reactors, but contain a draft tube which improves circulation and oxygen transfer and equalizes shear forces in the reactor.

The bubble size, rise velocity and the relative velocity between bubbles and microorganisms are important factors for gas transfer and fast moving bubbles and low bubble concentration limits cells contact with air/$CO_2$. Disadvantages with bubble reactors are related to the small surface-to-volume ratio and high energy requirement for stirring and internal illumination limited light flux, insufficient mass transfer and fluid dynamics, and heat build up from sun and/or artificial lighting. In an air lift reactor, light flux decreases exponentially with the distance from the irradiated surface. The algae near the light source are thus exposed to a high photon density, which enhances the growth rate, as compared to the cells at the center of the ALR tube, which receive less light as a result of shading and therefore grow more slowly. FIG. 20 illustrates the basic structure of a transparent vertical column/airlift bioreactor and system design and a reactor with internal illumination.

Flat-plated photobioreactors are made of transparent plastic or glass material. The large illumination surface area allows high photosynthetic efficiency, low accumulation of dissolved oxygen concentration, and immobilization of algae. The reactors are inexpensive and easy to construct and maintain and are suitable for outdoor cultures. However, the large surface area presents scale-up problems, including difficulties in controlling light conditions at high culture densities, temperature and carbon dioxide diffusion rate, and it is a tendency for algae adhering to the walls.

The vertical flat plate photobioreactors are equipped with coils for water cooling and perforated pipes for mixing and aeration of the cell culture. In addition, the unit is equipped with connections for adding culture medium, ventilation of dissolved oxygen, harvesting and spray cleaning of the interior. Scale-up may require many compartments and support materials. It has been reported some difficulties in controlling culture temperature and some degree of wall growth. A flat plate vertical rectangular transparent photobioreactor is shown in FIG. 21.

The flat thin layer open photobioreactor has a high surface-to-volume ratio of up to 170 per meter. It consist of two inclined rectangular glass lanes each 28 m long and 4 m with a total surface are of 224 m². The total culture volume in the bioreactor is about 2000 L. The inclination is 1.7%, providing a thickness of algal culture layer of about 6 mm and a flow velocity of 60 cm/sec. The suspension is drawn from a retention tank by a pump and evenly distributed at the top of the inclined glass area through a perforated polypropylene tube and flows by gravity back to the open retention tank for recirculation until harvesting.

Due to its thin culture thickness during light exposure and high energy efficiency of about 6.5%, the system has a reported high linear growth rate and biomass densities of about 40 g/dw/l (40 gram dry weight per liter), corresponding to an areal density of 320 g/dw/m². The system is easy to clean. However, the open design may cause high evaporative losses, diffusion of carbon dioxide to the atmosphere, contamination risk, temperature fluctuation, and is not able to sustain an optically dark zone to effectively prevent saturation and photoinhabitation. FIG. 22 illustrates a flat inclined thin layer photobioreactor.

There are major limitations with current PBR technologies and their design to meet requirements for high capacity biomass production. The most important factor that limits productivity is the cells or microorganisms access to the light quality and intensity level of photon energy that need to be large enough to initiate and support optimal growth. This is especially challenging when the cell concentration increases to a level where mutual blocking of light occurs. It has been stressed that uniform distribution of appropriate light conditions to each cell in the culture is needed to pave the ground for high capacity production of biofuel from microorganisms. Scale-up of small PBR's has also been reported as challenging and in some cases impossible.

Several proposals to improve the productivity have been introduced in different review papers. They have focused on the difficulties in providing improved light penetration in high density cultures and have suggested reducing the depth of the culture thickness in ponds, the tube diameter in tubular systems, and the distance between the parallel walls in flat plate PBRs. In addition, it has been proposed to implement flashing light, manipulate the algae antenna systems (the pigment's light receiving or light absorbing system), and increase mixing to prevent saturation and inhabitation, optimize the supply of $CO_2$ and nutrient to meet higher level of irradiation and to adjust the cultivation procedures to improve growth rates.

However, efforts to reach higher productivity with current technologies are sometimes difficult because of the interaction between factors involved. Higher mixing to bring cells to the surface for irradiation creates shear forces that can damage the cells and the energy consumption needed for operation increases significantly. Reducing the culture thickness is only practical down to a certain level, and when the culture thickness is reduced the culture density increases and will require higher mixing energy to bring more cells to the surface for irradiation. Higher cell concentrations will also require higher photon energy that may result in light saturation, inhabitation and damage to the cells. More intense mixing and higher light intensity will also reduce the cost efficiency of the operation and mixing does not determine the time each cell is illuminated and at what level.

Technically it has been a problem with high frequency flashing using conventional fluorescent light bulbs/tubes due to the time it takes for a lamp to light up and shut down. The LED technology, however, makes it possible to turn on and off the light at recommended frequencies, but the thickness of high concentration cultures needs to be kept below about 10 mm and therefore puts severe limitation on design and capacity of a system.

Interacting problems and bad engineering designs have caused many attempts at scale-up to fail, most notable the installations in Santa Ana, Murcia, Spain and La Rioja, Argentina. The following lists the major disadvantages with open pond, flat plate, tubular and bubble/airlift bioreactor systems. It should be noted that production of biofuel from microorganisms are in an early development stage. The following is a summary of the limitations with the current PBR technologies listed for each system:

Open Ponds
 Poor vertical light penetration resulting in low volumetric productivity
 Difficult to keep the environment constant at optimal growth conditions
 Impossible to control contamination and diffusion of $CO_2$
 High evaporative losses
 High volume of water magnifies the cost of processing/harvesting/separation
 Low mass transfer rates due to inefficient stirring resulting in low biomass productivity Require large areas of land Limited surface-to-volume ratio Tubular PBR Limitation in light penetration Limited mixing of culture in the light absorbing section result in inefficient gas transfers that can lead to inhomogeneous conditions and too high oxygen levels The shape and diameter of the tubes and thickness of culture create light and dark zones resulting in limited growth.

A continuous exposure of the culture to sunlight creates heat and requires cooling of the culture medium Intense sunlight may result in light saturation and inhabitation Bubble/Airlift PBR Limitation in light flux Insufficient mass transfer and fluid dynamics Heat from sun and/or artificial lighting builds up in the culture.

Non-homogeneous growth due to decrease in penetration of artificial light is causing the algae near the light source to receive higher photon density than cells further away from the light source (light flux decreases exponentially with the distance from the irradiated surface).

Flat Plate PBR

Limited control of high irradiation

Expensive constructions compared to ponds

Many separate units

Thus there has existed a long-felt need for a system and method for high capacity production of biomass.

SUMMARY OF THE INVENTION

This invention is designed to optimize growth and productivity of marine microorganisms for use of the biomass as a renewable fuel source and/or feedstock for products in the pharmaceutical and nutrient sector. Due to its special capabilities in treatment of cells within droplets, the technology may also have applications outside the area of producing biomass, including the medical field.

The advantages, improvements, and objectives of the light absorbing droplet unit are:

The PBR combines the functions of irradiation, mixing, gas transfer and gas exchange in one single unit that simplify the construction and operation of PBR.

The air chamber can hold gas concentrations that far exceed the level that can be dissolved in water, eliminates the solubility limitations of gases in water.

The higher concentration of $N_2$ in air (78%) and the higher $CO_2$ concentration that air can contain than water, combined with large surface area increases diffusion rates and supply of $CO_2$ and $N_2$.

The spray nozzles create micron size droplets that reduce the thickness of the culture during irradiation.

The droplets significantly increase the culture surface area and improve gas transfer and diffusion capabilities.

The method of irradiation of droplets provides optimal photon level and minimizes saturation and photoinhabitation.

The passive and active flashing creates light and dark zones and improves photosynthetic and energy efficiencies.

The energy efficient system uses a combination of sunlight and high efficiency LED artificial flashing light.

Simultaneously flashes red and blue light to increase rate of photosynthesis

The reflection and refraction in droplets reduces mutual shading and blocking of light to cells and therefore maximize growth during the culture's escalating cell density.

Irradiation of droplets in an air filled unit where the air is the continuous phase reduces loss of photon energy increases photosynthetic and energy efficiency, and growth.

Higher access to $CO_2$ and nutrients will increase photosynthesis and maximize growth.

The number of cells and their average size within a droplet can be established automatically and makes irradiation of a given number of cells possible with the photon flux density required.

The method of irradiation minimize light saturation and inhabitation and initiate and optimize the photosynthetic reactions at a lower energy level compared to current PBR's.

Adjustments of the amount and combination of gases in the droplet chamber makes $N_2$ starvation possible.

Uses LED lights in selected wavelengths to irradiate cells in droplets.

The light system includes an innovative combination of two passive and one active generated flashing method.

The dramatic increase of the culture surface area by making droplets and circulation of the cell culture is creating a dynamic surface area that is in several orders of magnitude larger than the static surface areas of ponds and current PBRs.

The large dynamic surface area makes it possible to reduce the facility footprint and amount of water in the PBR system. This reduces the investment, fluid handling and separation costs compared to the huge footprint and quantities of water used in ponds and other low density systems.

The droplet PBR is the only system that can process a huge number of individual cells including irradiation of cells at selected energy and photon levels (light wavelengths), supply of $CO_2$ and nitrogen at quantities adjusted to required consumption needs during the cells entire life cycle.

The very high liquid surface area of the droplets significantly improves the area of interaction between the water and the surrounding air and makes it possible to supply higher quantities of $CO_2$ and nitrogen needed for the cells to sustain the rapid growth (as a result of the reduced cell thickness and improved and optimized light conditions).

The level of $CO_2$ and nitrogen can be dissolved in the air filled droplet unit is much higher than in water, making the droplet unit independent of the solubility restrictions of $CO_2$ and nitrogen in the water column. This may result in faster and higher uptake of gases and lead to faster growth rates.

Surfactants can be used to increase diffusion rates by reducing surface tension at the air-liquid interface and at the liquid-cell membrane interfaces of microorganisms.

Treatment with chemicals and/or other agents to increase diffusion rates or biological reactions including stimulation of the cells own method in using hydrophobic and oelophilic substances to enhance intake of $CO_2$ by removing boundary layer resistance to $CO_2$ diffusion (membrane built up of silicone are hydrophobic).

The enhanced effectiveness of irradiation allow for operation of a significantly higher cell concentration than is possible in current PBRs without the typical cell blocking effect.

The high density that can be produced in the system will reduce the cost of operation, harvesting and centrifugation.

Even though light can be blocked within a droplet containing cells, the phenomena of refraction of light inside a droplet will reduce the blocking effect and the loss of energy in the ultra thin droplet is minimal according to Beer's Law.

The PBR is using a combination of solar and high efficient low intensity lighting.

Provide light treatment of selected number of cells by adjusting droplet size

Significantly reduces power consumption by selectively using sunlight, and/or red and blue LED in combination with white LED lights Use of droplet and droplet spreading to make use of low intensity grow light possible (400 ft.c) and thus reducing risk of light saturation and inhabitation Combination of the bioreactor and gas exchanger functions in the chamber that reduces risk of oxygen and nitrogen poisoning The use of enzymes to increase rate of photosynthesis Use of ultrasound or microwaves to retrieve carbohydrates from cells A method to produce microorganisms for food production in space or other weightless environments where droplets can stay in a chamber without falling to the ground by using The advantages, improvements, and objectives of the solar bio panel are:

The prototype solar bio panel of 0.2 $m^2$ creates dynamic surface areas per day that is larger than the surface area of a standard 1000 $m^2$ ponds.

The small surface area of the solar panel is reducing the need for artificial light equipment, and reduces the need for cooling of the cell culture due to unintended heating of large surfaces in warm weather with high sun radiation.

The panel can be operated in tilted positions to improve light efficiency from solar radiation by reducing reflection and improving light penetration through the culture of microorganisms.

The large dynamic areas and small footprint reduces the need for land area.

The thinner panel and higher cell concentration reduces the volume of water needed to grow microorganisms.

Higher cell concentration and less water reduce operational costs and makes processing and handling less time consuming.

Reduces the surface are for light exposure needed to grow microorganisms

Thickness of culture being exposed to light is always limited to bioreactor thickness.

The system provides a highly controllable environment for growth.

Reduced need for cooling because heating of culture is limited (the culture is stored in dark tank and exposure to light is dependent on cycles). In addition, the actual surface area is limited in size (a fraction of open pond designs)

Zigzag flow combined with passive and active flashing light creates multiple pulsing of cells as they pass through the panel.

Number of pulses caused by the special passive design can be adjusted by changing the pump capacity.

Injection of gases on the suction side of the pump creates high concentration of small bubbles that increases contact area between cells and $CO_2$.

Use of droplet spray in the gas exchange area in the culture's holding tank improves gas transfer and growth conditions.

Active flashing by use of horizontally or vertically positioned energy efficient LED spot lights increase growth and reduces saturation and photoinhabitation.

The flow channels are made of non-transparent bafflers to separate illumination of each flow channel.

Cells passing each "window" followed by the dark area in between, will experience rapid light-dark periods determined by the fluid velocity. In addition, flashing light-emitting diodes (LED) are used to generate higher frequency flashing.

The combination of the two PBR units, the light absorbing droplet unit and the solar bio panel, controls duration of irradiation and photon energy levels required to improve growth rate and increases productivity of microorganism cultures.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE FIGURES

The accompanying drawings, which are incorporated in and form a part of this specification, illustrate embodiments of the invention and together with the description, serve to explain the principles of this invention.

FIG. 9 shows photosynthesis per unit light as a function of the time the light was on.

FIG. 11 shows solubility of CO2 in water at one atmosphere with increasing temperature.

FIG. 12 shows solubility of nitrogen (FIG. 12A) and oxygen (FIG. 12B) in water at one atmosphere and different temperatures.

DETAILED DESCRIPTION OF THE INVENTION

Figure 1:
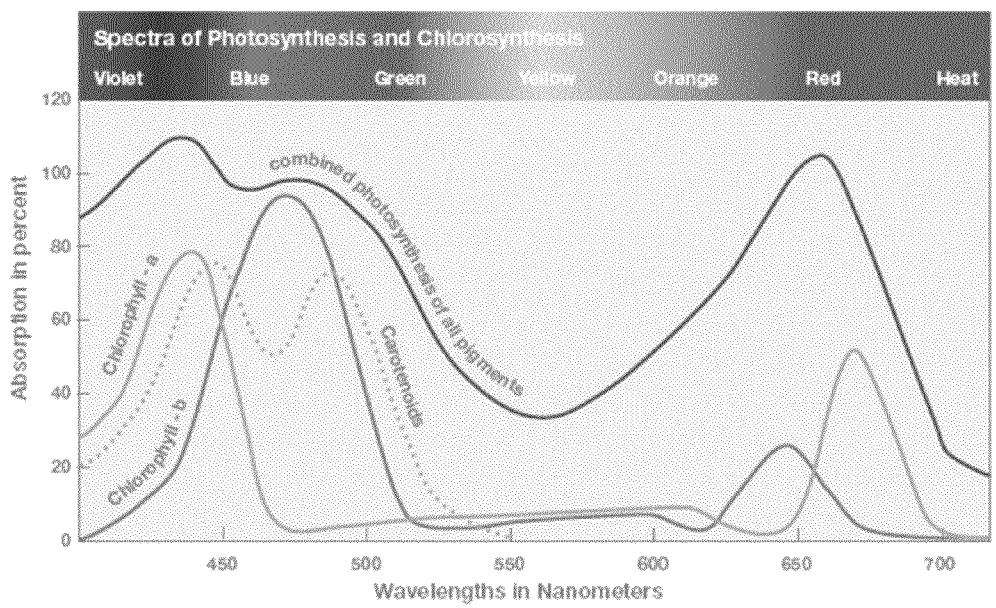
FIG. 1 illustrates absorption of light for chlorophyll and Carotenoids pigments at various wavelengths.
Figure 2:
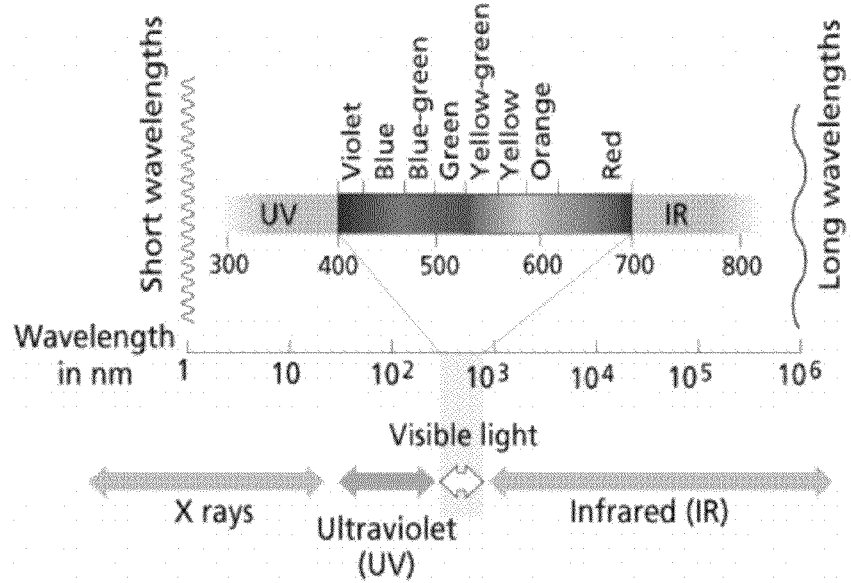
FIG. 2 illustrates wavelengths for x-ray, ultraviolet (UV), visible light, and infrared radiation.
Figure 3:
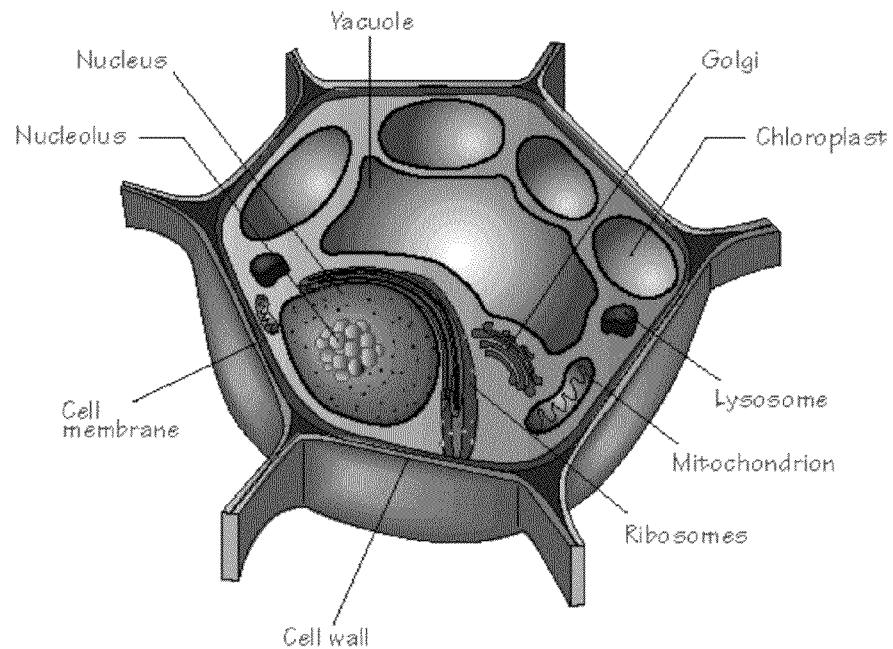
FIG. 3 illustrates a eukaryote cell showing the location of chloroplast.
Figure 4:
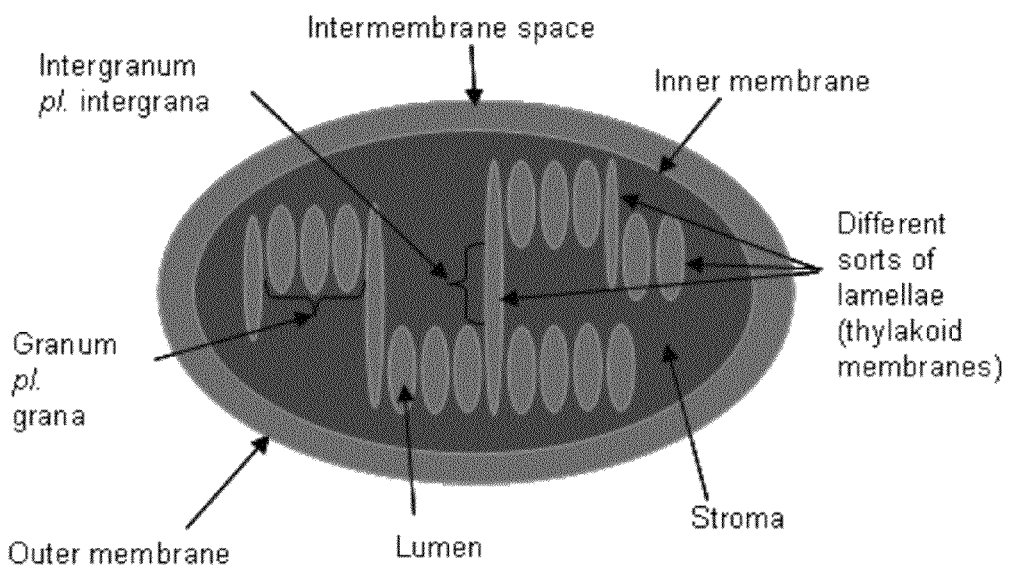
FIG. 4 illustrates the structure of chloroplast and its membrane structure.
Figure 5:
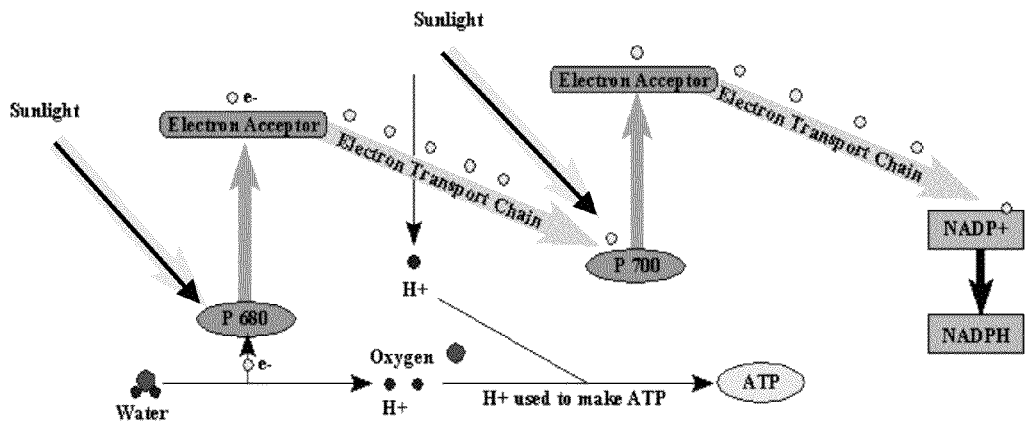
FIG. 5 shows the light-dependent reactions of photosynthesis at the thylakoid membrane.
Figure 6:
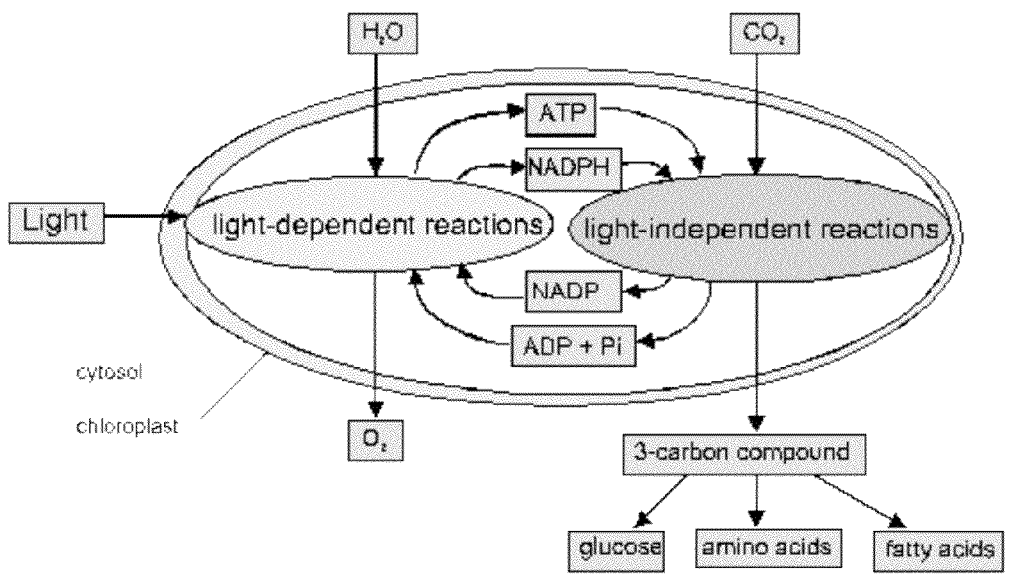
FIG. 6 illustrates the light and dark reactions in photosynthesis.
Figure 7:
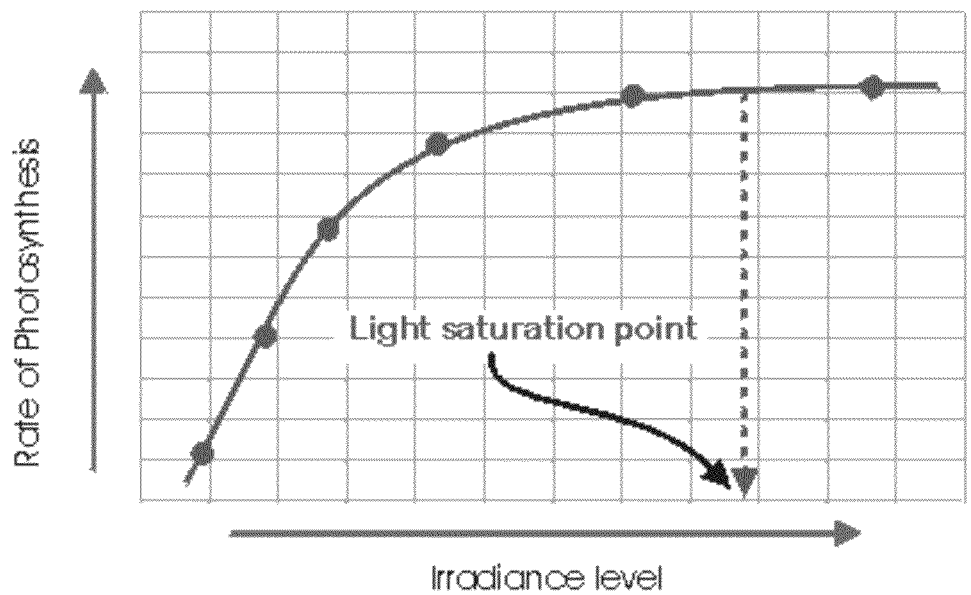
FIG. 7 shows light saturation point as a function of the rate of photosynthesis and level of irradiance.
Figure 8:
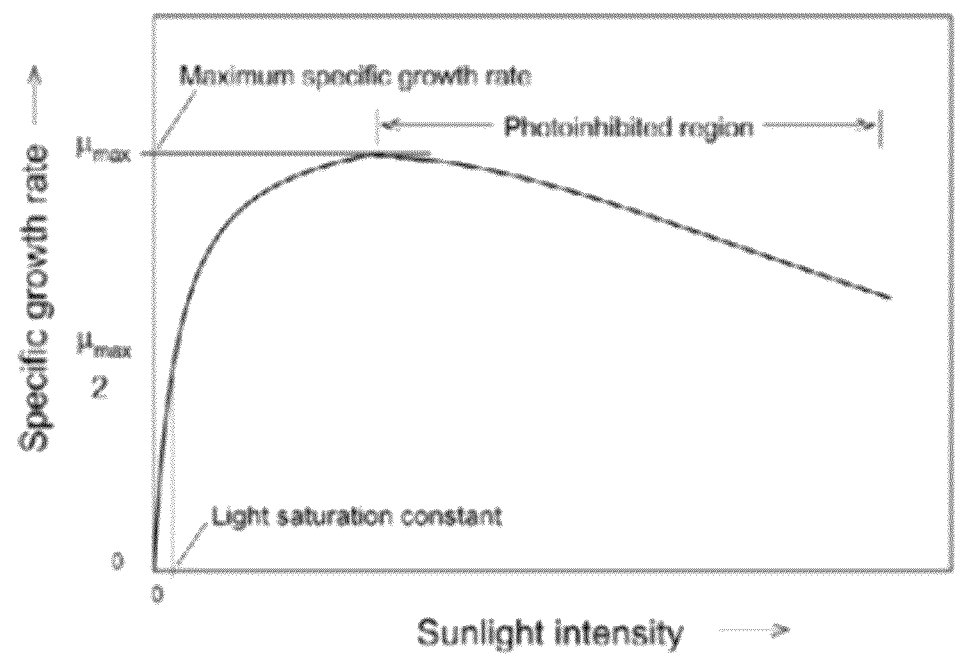
FIG. 8 shows the specific growth rate as a function of sunlight intensity.
Figure 9:
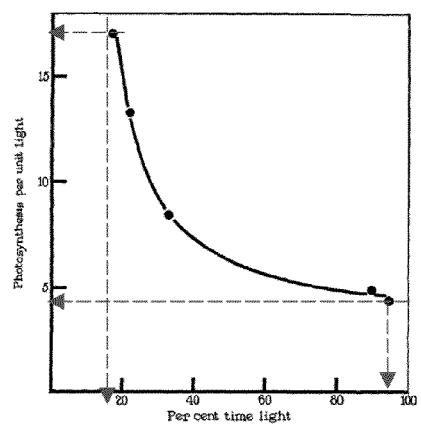
Figure 10:
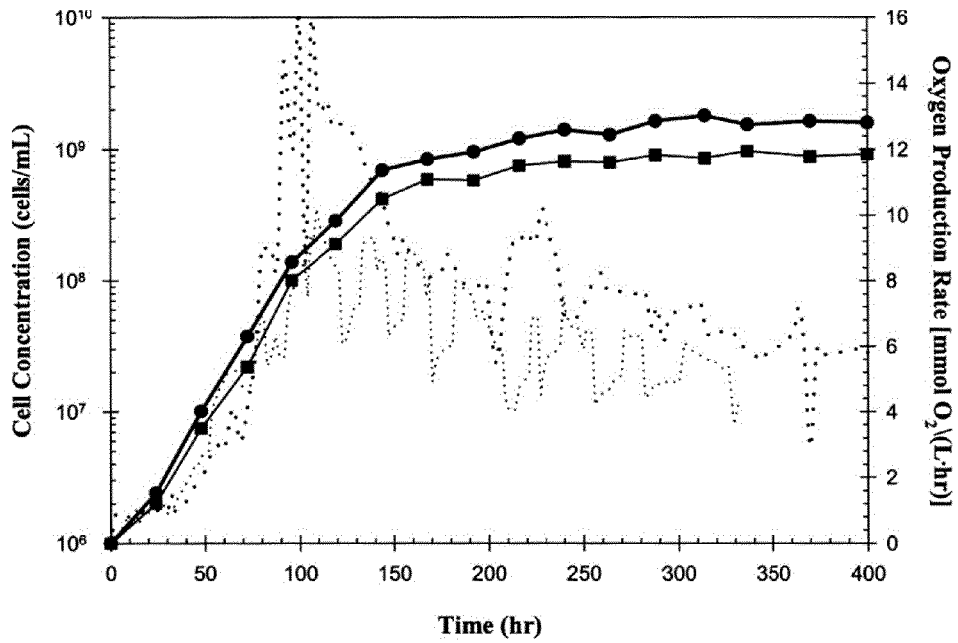
FIG. 10 shows of typical growth curves from two different flat plate laboratory PBRs with dotted lines representing oxygen production rates.
Figure 13:
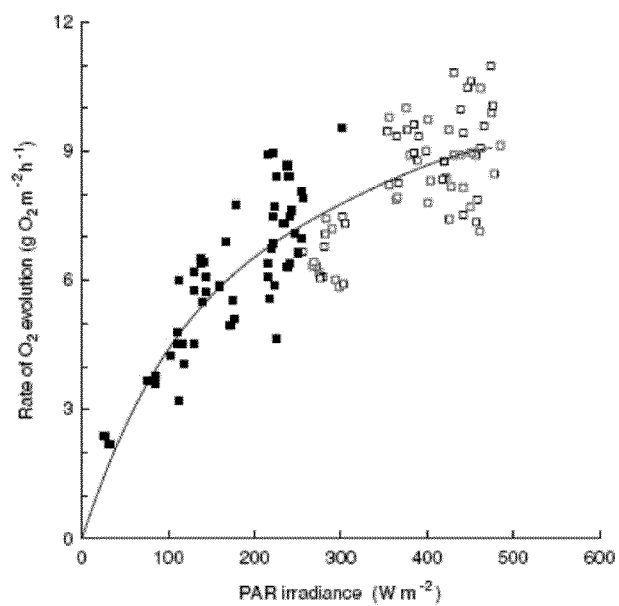
FIG. 13 shows net rate of oxygen evolution per square meter per hour of culture area at various PAR irradiances.
Figure 14:
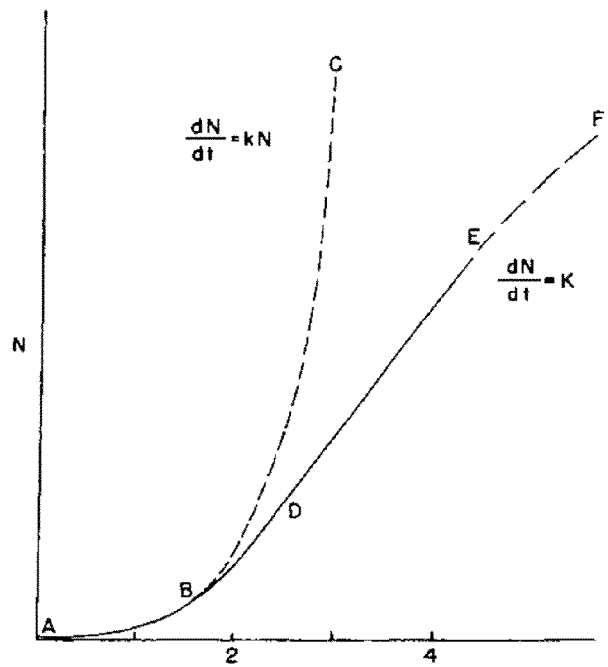
FIG. 14 shows a growth curve from growth experiments with *Chlorella* green algae.
Figure 15:
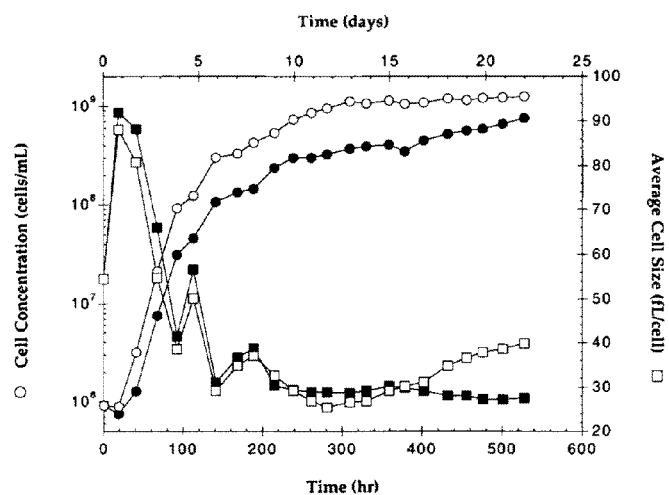
FIG. 15 shows growth curves (○ and ● cells/ml) and corresponding average cell sizes (□ and ■ fL/cell) in two different light intensities.
Figure 16:
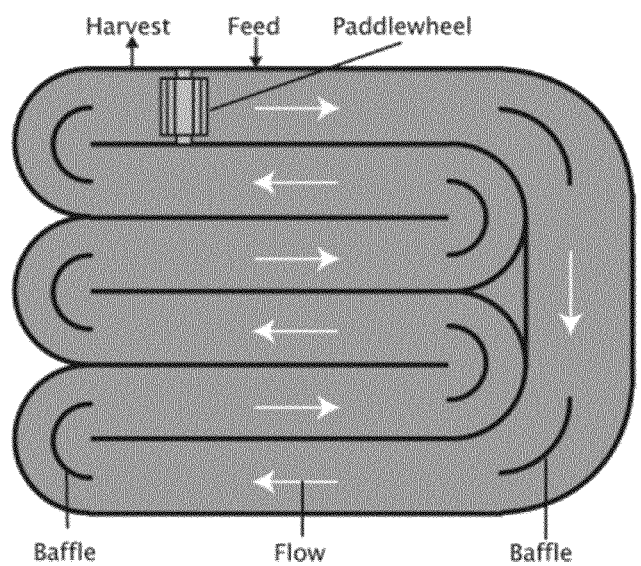
FIG. 16 illustrates a raceway pond.
Figure 17:
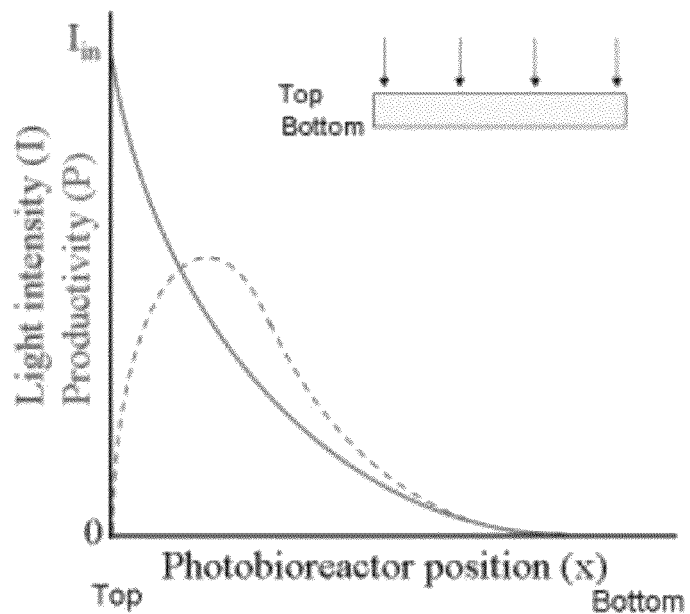
FIG. 17 shows light intensity (solid line) and productivity (dotted line) in an open pond at high light intensity.
Figure 18:
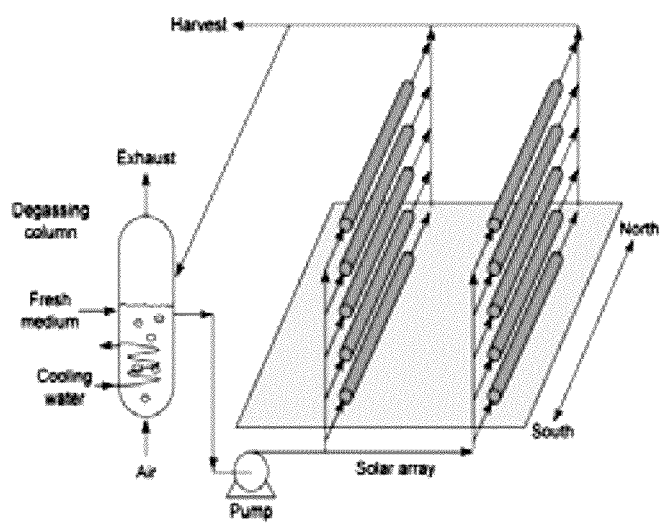
FIG. 18 illustrates a tubular photobioreactor system.
Figure 19A:
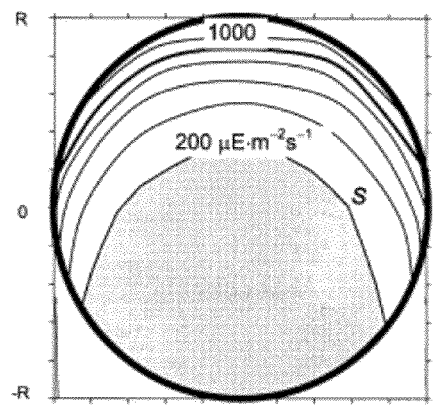
FIG. 19A shows irradiance profiles inside a 0.06 m diameter transparent tube
Figure 19B:
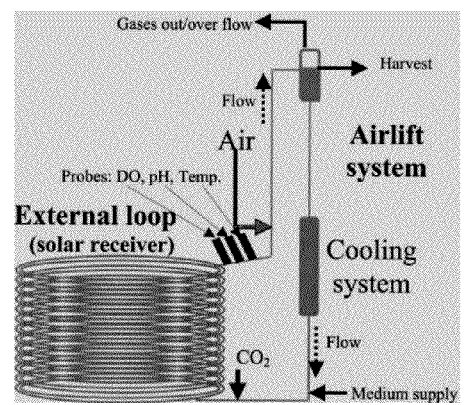
FIG. 19B illustrates a specific helical coil tubular design including a circular coil of transparent houses for irradiance.
Figure 20A:
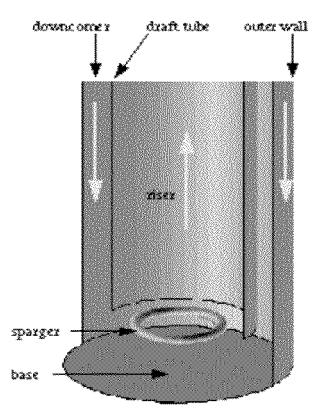
FIG. 20A illustrates a basic vertical column/airlift bioreactor and FIG. 20B shows a system design including an external circular coil of transparent houses.
Figure 20B:
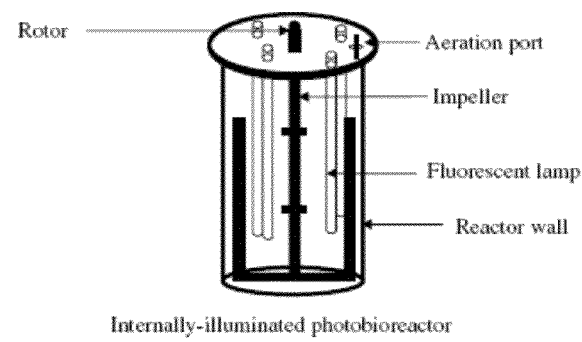
Figure 21:
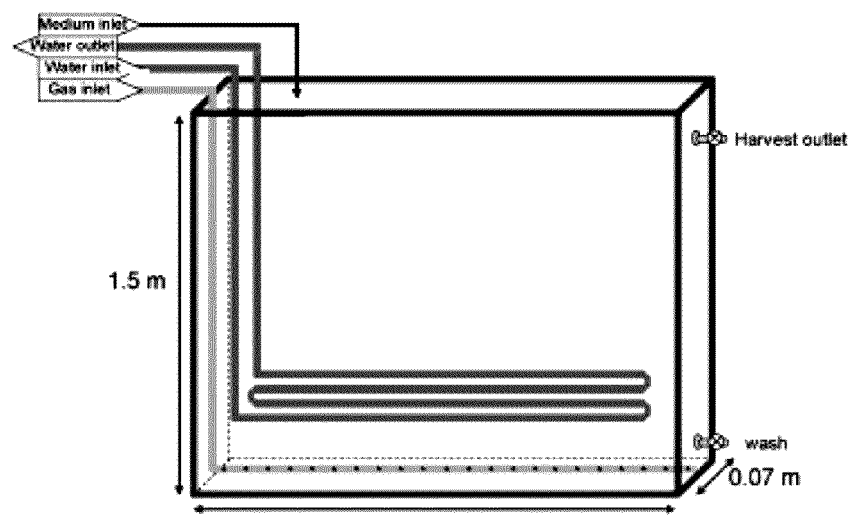
FIG. 21 is a diagram of a flat plate vertical photobioreactor.
Figure 22:
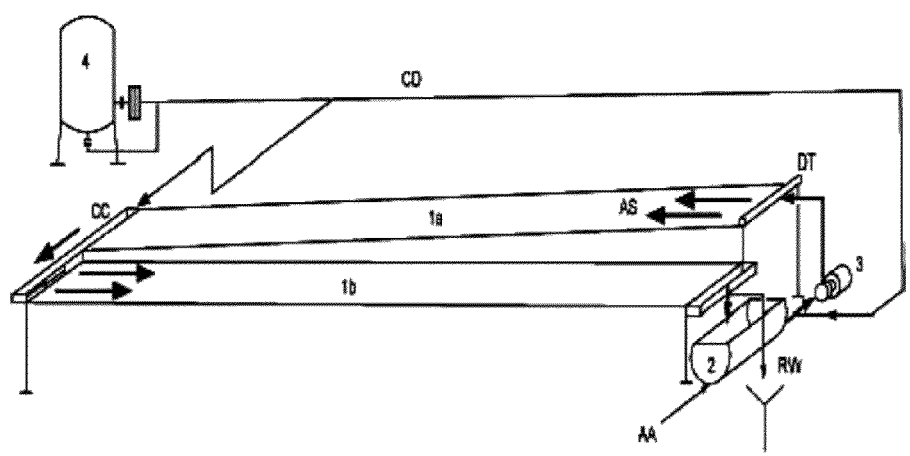
FIG. 22 illustrates a flat inclined thin layer photobioreactor.

Many aspects of the invention can be better understood with the references made to the drawings below. The components in the drawings are not necessarily drawn to scale. Instead, emphasis is placed upon clearly illustrating the components of the present invention. Moreover, like reference numerals designate corresponding parts through the several views in the drawings.

This invention is using circulation of autotrophic microorganism between a dark holding tank containing the culture of microorganism, and two transparent light absorbing units including a thin flat solar bio panel and a light absorbing droplet unit. The two photobioreactor units are interconnected and can be operated independently, in series or in parallel depending on the cells' needs for treatment to achieve optimal growth.

Figure 23:
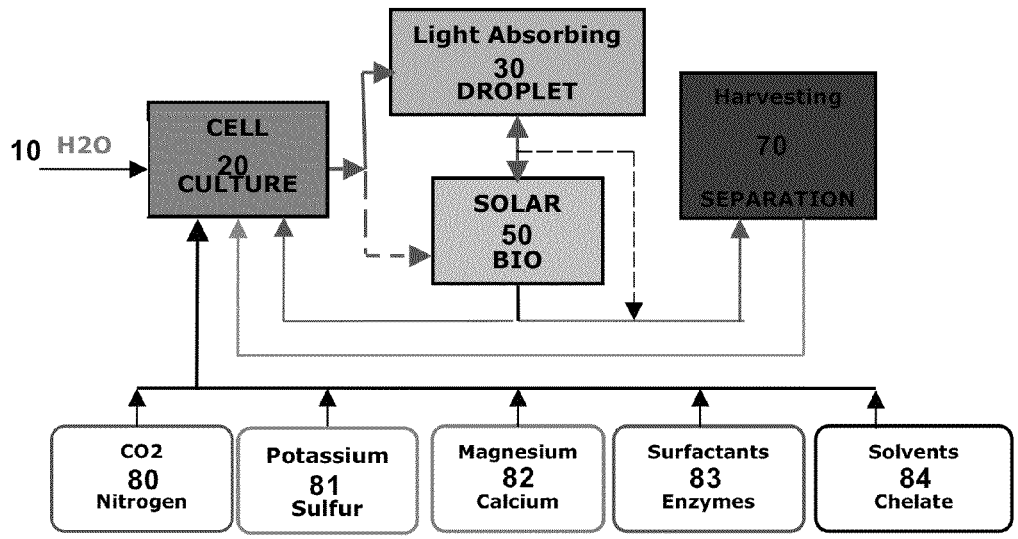
FIG. 23 is a process flow diagram of the photobioreactor system.

FIG. 23 is a process flow diagram of the photobioreactor system. The tank containing the microorganisms referred to as the cell culture 20 is connected to an external source of water 10, fresh water or seawater, and a pump for circulation of the cell culture. The system is powered by electricity from the grid of from separate renewable energy sources such as wind and solar power combined with fuel cells. In addition, pressurized air, $CO_2$ and/or $CO_2$ enriched air 80 is added to the suction side or the pump and mixed into the water by the pump's impeller before entering the solar bio panel and/or the droplet light absorbing unit. Pure $CO_2$ or $CO_2$ 80 enriched air can also be supplied directly to the spay nozzle or into the droplet chamber. Highly water soluble nutrients and other growth stimulating agents are mixed into the water by recirculation. These may include, but are not limited to: nitrogen 80, phosphorus, potassium and sulfur 81, ammonia, urea, magnesium and calcium 82, iron. In addition, the invention may include technologies for the use of surfactants, enzymes, chemical and coating agents to increase photo reactivity 84, membrane diffusion and growth rates, and agents to prevent fouling and cell adherence to the inside of transparent walls.

For harvesting, the culture medium is transferred to a separate unit 70 for separation and oil extraction, and the remaining nutrient rich fluid is returned to the tank for reuse.

The growth and harvesting process will be controlled by sensors that measure parameters important to obtain maximum growth and to automatically add required nutrients and other growth stimulating agents when needed. The sensor system may also redirect the flow of cell culture to the processing unit at preset values for harvesting, separation, oil extraction or for specific biomass treatments.

This invention includes improved methods and technologies for high capacity production of biomass including use of droplets to increase the surface area of the cell culture. The increased surface area optimize mass transfer, gas exchange, diffusion, and irradiation known to be limiting growth factors in current ponds and PBRs. The method of irradiation of droplets minimize saturation and photoinhabitation and meets the need to provide each cell with the photon energy, light and dark zones, $CO_2$ and nutrients required to initiate photosynthesis and maximize growth. This will greatly improve the photosynthetic and energy efficiencies, reduce mutual shading and blocking of light to cells and therefore maximize growth during the time of the culture's escalating cell density. The two solar absorbing units are using a combination of solar and high efficient low intensity light emitting diodes (LED) lighting or similar high efficiency lighting. The irradiation takes place when the cell culture is circulated via the bio droplet light absorbing unit and/or the thin solar bio panel.

The high interfacial area created by transforming the culture into droplets provides excellent conditions for increased air to liquid and fluid to cell membrane diffusion rates, biochemical reactions, and gas and heat transfer. To optimize the growth conditions, the two light absorbing units have different primary functions. The thin solar bio panel 50, or a flat panel unit, generates a large dynamic surface area for irradiation of the culture and regulates the duration of light exposure. The droplet light absorbing unit 30 provides excellent conditions for irradiation of individual cells located inside the droplets, mass transfer of gases and $CO_2$ enriched air. Operation of the units in series, parallel or independently depends on the growth phase and the specific need for light, air, $CO_2$ and nutrients. The advantages of the PBR system technologies and the two photobioreactor systems are described below in more detail.

Figure 24:
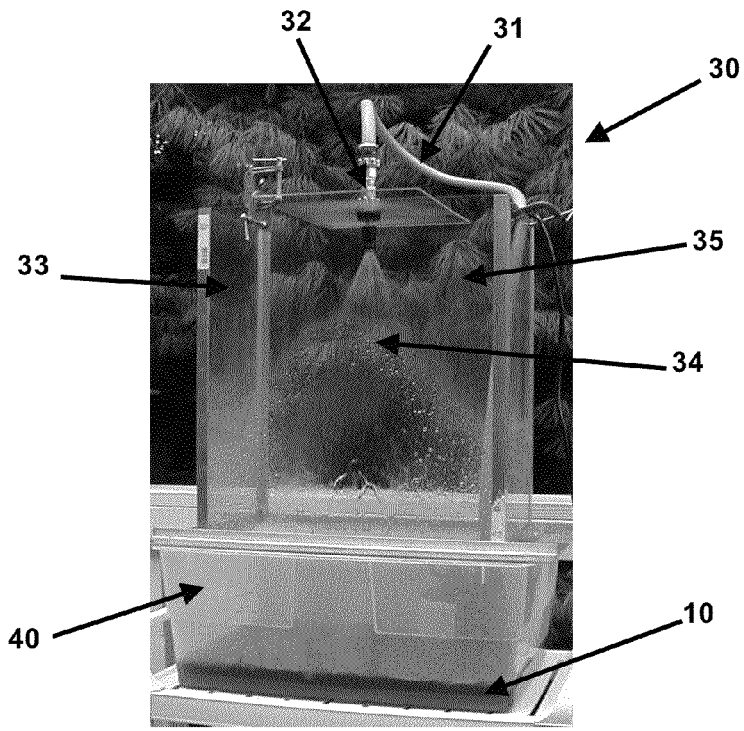
FIG. 24 is a photograph of a test prototype used during proof of principle testing.
Figure 25:
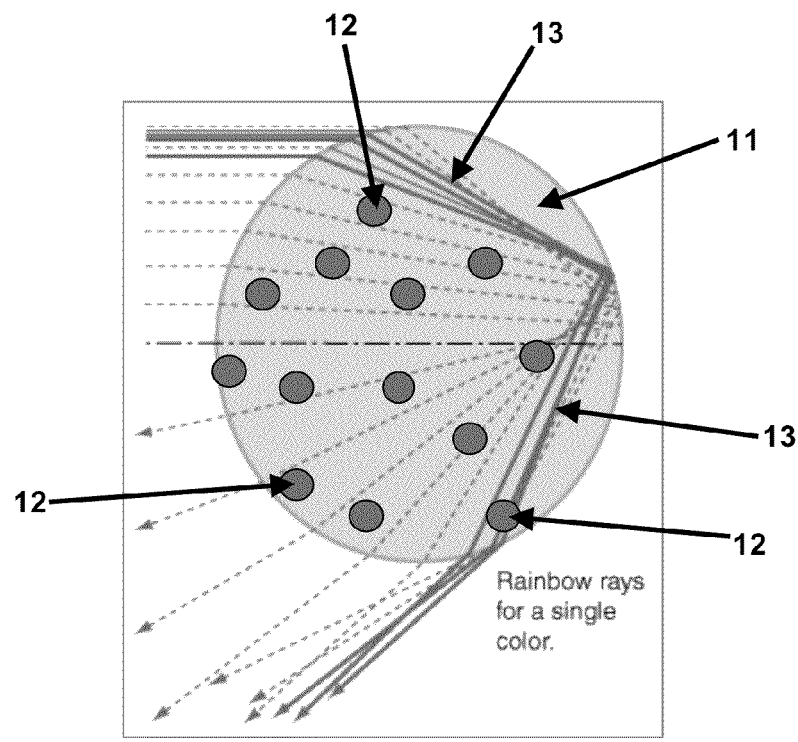
FIG. 25 illustrates light paths in a 250 μm droplet containing micro sized cells.
Figure 26:
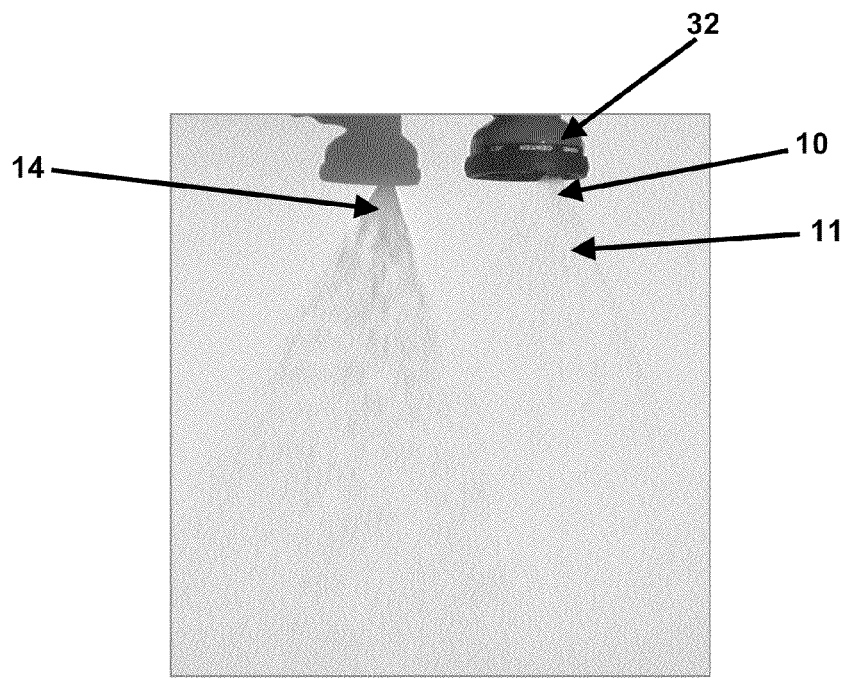
FIG. 26 is a photograph of solar radiation through a flat spray pattern.

The Light Absorbing Droplet Unit: FIG. 24 is a photograph of a test prototype used during proof of principle testing. Irradiation of cell cultures in current PBRs are done with cells suspended in the fluid with the fluid being the continuous phase. The fluid is causing loss of photons by reflection, absorption and scattering, and the loss increases exponentially when the cell density and penetration depth (culture thickness) increases. The photon energy that does not reach the cells is lost and converts into thermal energy that heat up the culture. The light absorbing droplet unit 30, however, is an air filled chamber where the air is the continuous phase. This significantly reduces loss of photon energy and makes the unit even more energy efficient by combining irradiation of droplets containing cells with mass transfer, gas exchange, mixing and temperature control into one single and simple design, that does not require separate gas exchange units, mixing devices or sparger systems.

The light absorbing droplet unit 30 includes a chamber 35 made from four transparent walls 33. Water 10, with microorganisms suspended therein, is pumped from a holding tank 40 through a tube 31 and forced through a nozzle 32. The nozzle 32 sprays the water 10 into the chamber 35, wherein droplets of water 10 with suspended microorganisms are created.

The droplets are, in reality, converting the algae suspension into μm size droplets that dramatically increases the culture surface area and creates a super thin layer, equal to the droplet diameter. The thin layer is reducing the thicknesses of the culture by several orders of magnitude compared to thicknesses in current PBR systems that range from approximately 7 cm to 30 cm for flat plate, tubular or ponds.

The number of cells and their average size within a droplet can be established automatically by continuously counting the number of cells in a given volume of suspension that equals the volume of the droplets created. This innovative method creates an opportunity to irradiate the given number of cells that can fit within a droplet with optimum photon flux density, and eliminates the need of using higher light intensity to penetrate deeper into cell cultures to irradiate an unknown number of cells. The method of irradiation will therefore (1) minimize light saturation and inhabitation and (2) initiate and optimize the photosynthetic reactions at a lower energy level compared to current PBR's while at the same time eliminating energy consuming mixing/stirring to bring cells in and out of the illuminated surface.

The enhanced effectiveness of irradiation and following photosynthetic reactions of the cells will result in increased growth and productivity and in theory allow for operation of a significantly higher cell concentration than possible in current PBR's without the typical cell blocking effect in high density cultures. This will reduce the cost of operation, harvesting and centrifugation. Even though some light can be blocked within a droplet containing cells, the phenomena of refraction of light inside a droplet will reduce the blocking effect and the loss of energy in the ultra thin droplet is minimal according to Beer's Law. Air droplets can also be injected in a droplet to (1) reduce number of cells, and (2) to improve light penetration and cell irradiation.

FIG. 25 illustrates light paths in a 250 μm droplet containing micro sized cells. The size of cells 12 of microorganisms varies depending on species but is typically for green algae cells from about 5 to 50 microns depending of the stage of cell development. In addition to improved irradiation the cells 12 can be treated more efficiently in supplying the higher amount of $CO_2$, nitrogen, and nutrient required to optimize the photosynthetic reactions as a result of the improved irradiation. Improvements of cell irradiation can be illustrated using a cross section of a spherical droplet 11 showing the light path 13 of parallel light rays from entering a droplet containing cells. The volume of the droplet 11 can contain a much higher number of cells 12 than if they were spread out on the surface and the refraction and reflection phenomena of the light path provides light from different directions, thus reduces the shading effect known to prevent light penetration in dense cultures. FIG. 25 does not include light going through the droplet 11 on the back of the droplet 11.

The droplets 11 are formed when the air resistance exceeds the small surface tension forces of the water. The shear force acting on the cells 12 when leaving a nozzle is therefore limited compared to the shear forces acting on the cells during constant aggressive mixing of cell cultures to bring the cells to the surface for illumination, and to improve mass transfer. The size of the droplets 11 and the spray patterns can be varied and is depending on the water pressure and type of nozzle.

FIG. 26 is a photograph of solar radiation through a flat spray pattern. The nozzle 32 is spreading the water 10 in an angle creating water strings of micrometer (μm) sized droplets 11. The spreading results in open spaces between the strings where light can shine through. Light is also shining through the tiny droplets. The picture was taken against a white background when spraying water 10 at 5.67 Wm (1.5 GPM) and 55 psi from the red spray nozzle 32. The spray was held parallel and 5 cm away from a white wall. The shadow 14 to the left of the red spray nozzle, clearly demonstrate that, except for an area close to the nozzle, the solar radiation is penetrating the transparent spray pattern without leaving visible shadow.

The significant increase in the surface area by making droplets out of the cell culture is in several orders of magnitude larger than the static surface areas of ponds and current PBR's. The large dynamic surface area makes it possible to reduce the footprint of biomass production facilities and the use of higher cell concentrations reduces the amount of water needed for production. This reduces the investment, fluid handling and separation costs compared to the huge footprint and quantities of water used in ponds and other low density systems. Table 1 presents the droplet diameter of various droplets and the corresponding surface area and volume per droplet, the number of droplets per liter, and the total surface area per liter for various droplet diameters.

TABLE 1

| Droplet diam. Microns (μm) | Surface area of 1 droplet (Sq. mm) | Volume of 1 droplet (cu. mm) | Total droplet Count per liter | Total surface area per liter (sq. meters) |
|---|---|---|---|---|
| 1000 | 3.14 | 0.524 | 1,910,000 | 6.0 |
| 500 | 0.785 | 0.0655 | 15,300,000 | 12.0 |
| 250 | 0.196 | 0.00819 | 122,000,000 | 24.0 |
| 125 | 0.0491 | 0.00102 | 977,000,000 | 48.0 |
| 60 | 0.0113 | 0.000113 | 8,840,000,000 | 100 |

To illustrate the huge surface area created by a nozzle delivering 250 micron size droplets, only 41.7 liters of water is needed to create a 1000 $m^2$ (0.247 acres) surface area equal to the ponds built in Roswell, N. Mex., and if the selected nozzles had a capacity of 41.7 $m^3$/hour, the hourly surface area created would be 1,000,000 $m^2$ per hour equal to 247 acres per hour. It should be noted that the volume in each pond is 300,000 liters with a culture thickness of 300 mm.

The light absorbing droplet PBR can process a huge number of individual cells per hour. Assuming that each 250 micron droplet contains 30 cells and the pump capacity is 41.7 m3/h the number of cells that can be treated per hour is 152,622 billion. The processing include irradiation of cells at selected photon energy levels and quality (light wavelengths), and the supply of $CO_2$ and nitrogen at quantities adjusted to optimize cell development during their entire life cycle. The processing may also include treatment with chemicals and/or other agents to increase diffusion rates or biological reactions.

The greatly increased culture surface area improves the capabilities for mass transfer, gas exchange, diffusion of $CO_2$, $N_2$ and the removal of dissolved oxygen. The PBR can introduce pressurized $CO_2$ enriched air or pure $CO_2$ at the suction side of the circulation pump or directly in the spray nozzles or into the light absorbing air filled droplet chamber. The latter will allow for use of much higher concentrations of $CO_2$ in air and eliminates the solubility limitations of gases in water. When the gases are passed through the nozzle or the pump, the droplets will contain tiny $CO_2$ or $CO_2$ enriched air bubbles that in addition will increase diffusion and gas transfer and increase light penetration. The high $CO_2$ removal potential a result of increased photosynthetic efficiency makes the unit an interesting concept for flue gas mitigation from fossil fuel powered electricity facilities.

The PBR will include methods and technologies to increase diffusion rates in cell membranes to increase the cells uptake of $CO_2$, nitrogen and nutrients needed to sustain maximum growth. This may include the use of surfactants, chemical treatment and biocatalytic coating agents including stimulation of the cells' own method in using hydrophobic and oelophilic substances to enhance intake of $CO_2$ by removing boundary layer resistance to $CO_2$ diffusion (membrane built up of silicone are hydrophobic).

The PBR is by design an energy efficient system that uses a combination of sunlight and high efficiency LED artificial flashing light. The LED lights are capable of high frequency on-off flashing and are used in selected wavelengths at low output to extend the lifetime of the light system.

The light system includes an innovative combination of two passive and one active generated flashing method. The first passive method is a result of the recirculation of the culture between the dark tank and the droplet light harvesting units, resulting in a flashing light effect at frequency and duration determined by the pump capacity and volume of water in the tank. The second passive flashing is created when droplets are passing slim parallel light openings in the droplet light harvesting unit (or in the flow channels in the solar bio panel).

The flashing frequency is determined by the droplet or the fluid velocity and the duration of light and dark periods are determined by the width of the light opening perpendicular to the flow direction and the width of the light blocked out section. The light and dark sections are adjusted to provide recommended values where the dark period is about 10 times longer than the light period. The active flashing method uses fixed LED spot lights at the light openings to create a higher level of flashing than the passive methods or during low light conditions. The fixed and flashing lights are located on the outer surface of the transparent walls to reduce heating of the culture and to simplify maintenance. The intensity of the blue light can be adjusted in the period when chlorophyll synthesis requires high level of blue photon energy.

Figure 27A:
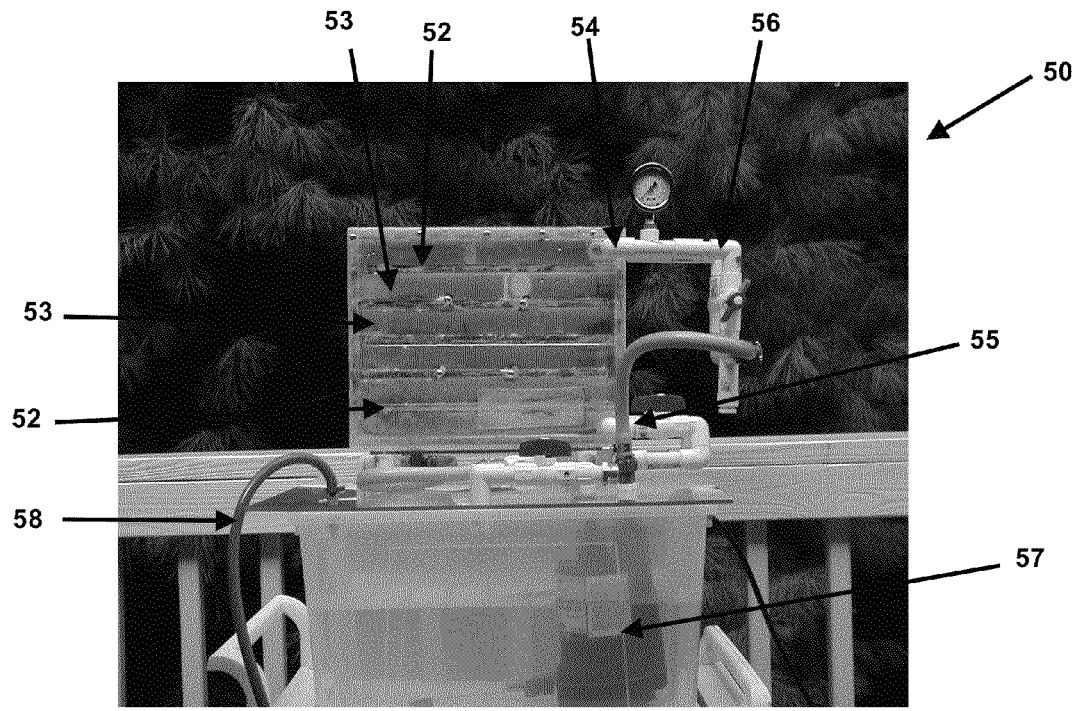
FIG. 27A is a photograph of the front of the solar bio panel located on top of a transparent tank including the pump for recirculation.
Figure 27B:
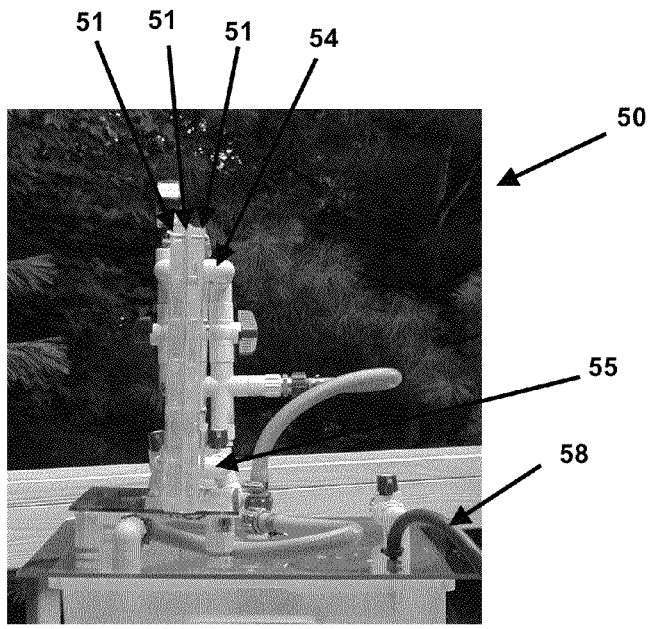
FIG. 27B is a photograph of the side of the solar bio panel.

The Solar Bio Panel: FIG. 27A is a photograph of the front of the solar bio panel located on top of a transparent tank including the pump for recirculation. FIG. 27B is a photograph of the side of the solar bio panel. The thin solar bio panel 50 has a flat sandwich construction of three transparent walls 51 kept apart by vertical and horizontal bafflers 52 creating narrow flow channels 53 and horizontal zigzag movement of the cell culture. The distance between the walls represents the thickness of the culture and the length of the flow channels determines the duration of irradiation. The slim design of about 10 mm wide flow channels increases productivity and allows light to penetrate through the culture even at higher cell densities and reduces the dark zones/areas where sunlight does not penetrate as observed in ponds and tubular design systems. This minimizes the need for use of high intensity light that may result in light saturation and photoinhabitation of the cells and damage to chlorophyll pigments needed for photosynthesis.

The panel has an inlet and outlet at the top and bottom, respectively, of the unit and is connected via pipes 56 to a pump 57 in the holding tank 40 with water 10 containing the culture of microorganisms that is continuously recirculated between the panel and the tank. $CO_2$ and/or $CO_2$ enriched air is injected on the suction side of the pump 57 and mixed into the cell culture as tiny air droplets. The culture medium is dropped back into the tank in a way that creates air bubbles and a larger air-water interfacial area. Use of spray nozzles in the gas exchange area in the storage/holding tank can further improve mass transfer, and the spray pattern can also be illuminated to create a second droplet light absorbing system in the holding tank. $CO_2$ enriched air is supplied through a hose 58.

The recirculation of the cell culture is creating a dynamic surface area for light exposure of cells that is several orders of magnitude larger than the solar panel itself and even larger than the surface areas of a standard 1000 m$^2$ ponds. In example, the effective light absorbing surface area of the test prototype was only 0.206 m$^2$ but created a 1,014 m$^2$ large dynamic area per hour at a pump capacity of 1.55 m$^3$/h or a surface area equal to 24 standard ponds per day. This significantly reduces the need for occupation of large land areas and the footprint is in order of magnitude less than that of a single 1000 m$^2$ pond.

The relatively small surface area and volume of the solar bio panel compared to the volume in the holding tank is also reducing the need for artificial light energy and light sources, and reduces the need for cooling of the cell culture due to unintended heating in warm weather with high sun radiation. The PBR can be operated in a vertical position or tilted to improve light efficiency from solar radiation by reducing reflection and improving light penetration through the culture of microorganisms.

The PBR and method of operation significantly reduces the volume of water needed compared to larger surface area systems. This reduces operational costs and makes processing and handling less time consuming. In addition, the large dynamic surface area and smaller volume of water results in a high surface-to-volume ratio, known as an important growth factor. The shorter light exposure reduces heat build-up from continuous solar irradiation and subsequent need for cooling.

The combined use of free sunlight and new high energy efficient LED, fluorescent, or advanced crystal laser light technologies with wavelengths corresponding to the red and blue artificial pulsed lighting, further reduces power consumption and costs of operation. The bioreactor system can also be powered by renewable energy (wind and solar) in combination with the use of fuel cells for electricity generation. The fuel cells can operate from hydrogen and/or oxygen produced by microorganisms and from electrolysis produced hydrogen from excess wind and solar power.

Figure 28:
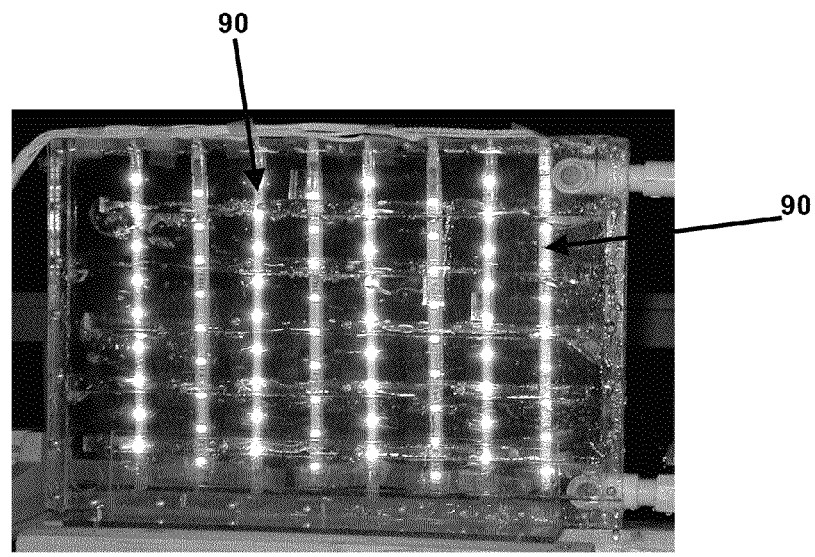
FIG. 28 is a photograph of horizontally mounted strings of LED lights for a double solar panel
Figure 29:
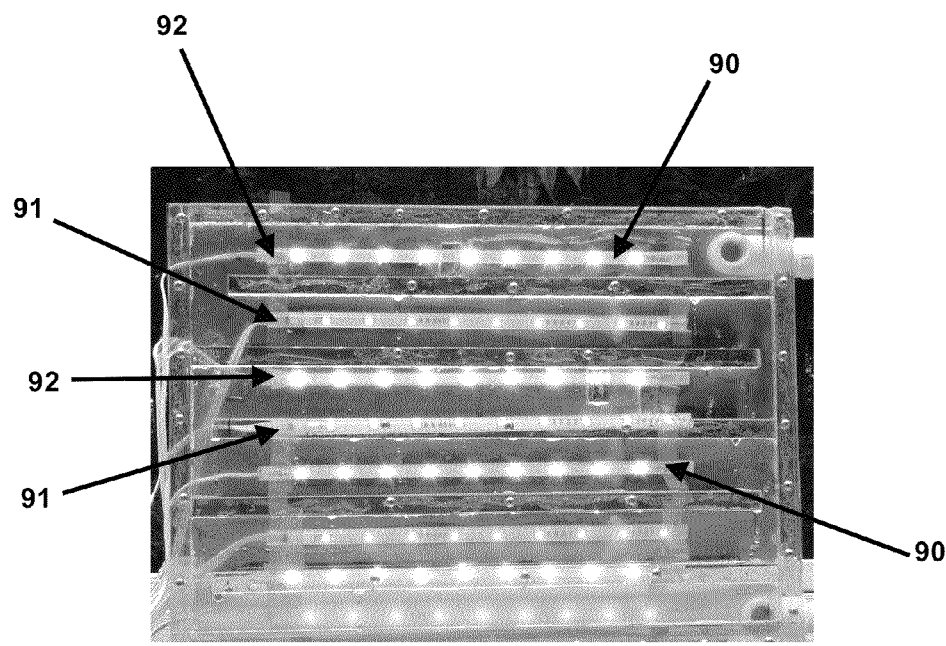
FIG. 29 is a photograph of vertically mounted strings of LED lights for a double solar panel.

FIG. 28 is a photograph of horizontally mounted strings of LED lights for a double solar panel. FIG. 29 is a photograph of vertically mounted strings of LED lights for a double solar panel. The PBR has two passive and one active pulsing system. The first passive pulsing system effect is a result of the recirculation of the culture between the dark holding tank and the solar bio panel resulting in a flashing effect with frequencies equal to the number of illuminated cycles per hour. The second passive pulsing effect is created when cells are passing fixed narrow light openings in the panel. The frequencies and the duration of the light and dark periods are determined by the distance between the light openings and the velocity of the cells passing the lights. The active flashing spot lights are superimposed to the passive pulsing and create a higher frequency of flashing. Light strings 90 are located on the outer surface of the transparent walls to simplify maintenance and replacement of lights and to reduce heat transfer to the culture. Each light string 90 can include LEDs that produce the same or different wavelengths of light. Further, different light strings 90 that emit the same different wavelengths of light can be used. For example, the light strings 90 can alternative between blue light strings 91 and white light strings 92. FIGS. 28 and 29 show strings of LED lights creating a number of separate white and/or blue flashing light spots.

The flow channels are made of non-transparent baffler to concentrate illumination of each flow channel. When the cells are passing each LED spots followed by the dark area in between, they will experience rapid light-dark periods determined by the fluid velocity and distance between the lights In addition, pulsed light-emitting diodes (LED) are used to superimpose automatic pulsing.

The harvesting unit may include use ultrasound to break cell membrane to simplify the extraction process of lipids.

Proof of Principle Testing

The Light Absorbing Droplet Unit: The prototype light absorbing droplet unit tested consisted of a partly closed and transparent rectangular container equipped with nozzle(s) for making droplets of the cell culture to (1) create interaction between the liquid and surrounding gas, (2) significantly increase the water and air interfacial area, (3) increase mass transfer/gas exchange rate, diffusion rates of gases for increased supply of $CO_2$ and nitrogen, (4) improve chemical and biological reactions when using treatment agents, and (5) create unprecedented conditions for illumination of individual algal cells cell culture. The PRB may be constructed in other shapes such as a cylinder, sphere, square, etc, depending on spray pattern to create maximum efficiency.

The light absorbing unit acts as a gas exchange chamber and was air ventilated using filters to minimize air pollution and to allow escape of excess gases. The nozzles at the top of the unit were connected to a pump located inside or outside of the reservoir that recirculates the culture of microorganisms. FIG. 24 shows a test prototype of the droplet PBR system with the rectangular shaped transparent light harvesting chamber located on top of a transparent plastic container. In this test set-up, the pump for recirculation of the culture of microorganisms was placed in the container.

The spray nozzles tested were located on the top of the unit spraying strings of water down into the tank. Nozzles can also be located at the bottom of the chamber and spray upwards to increase the time of exposure to light and gases.

A small test prototype of the droplet light harvesting unit was tested from Aug. 7, to Aug. 9, 2009. The purposes of the testing were threefold and designed to; (1) demonstrate that the concept could be used to significantly increase cell density, (2) determine if low intensity flashing red and blue and fixed white LED lights could be used at night to increase cell density, and (3) verify that hydrodynamic shear stresses created by the centrifugal pump and the nozzle did not damage or kill algae cells.

Environmental conditions: Sunrise: 6:19 am-Sunset: 8:08 pm (Approximately 14 hours of daylight and 10 hours of darkness), no clouds. Max temperature: 34° C., Minimum temperature: 23° C., Wind: Calm.

Figure 30A:
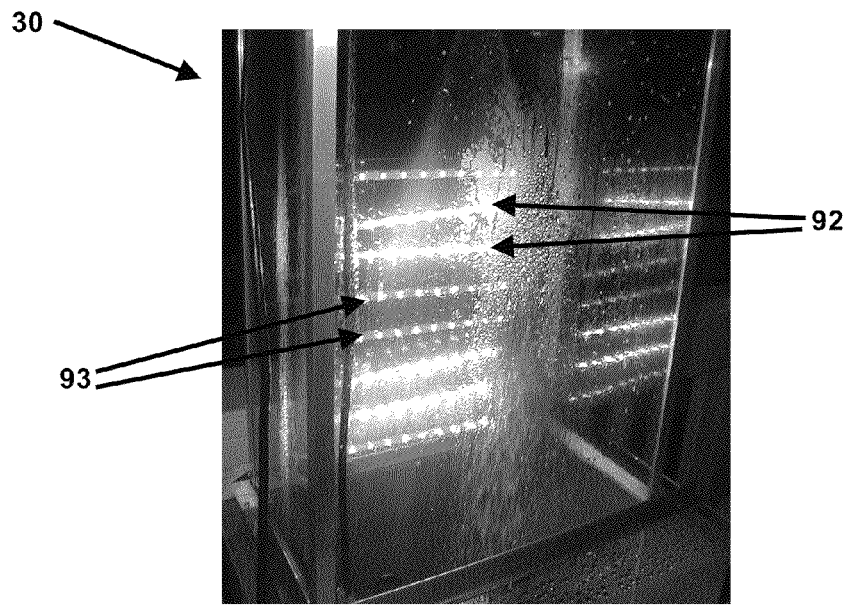
FIG. 30A is a photograph of the system used during testing with white and blue light strings located at the back and on the outside of the transparent wall and FIG. 30B is a photograph of the system used during testing with white and red light strings located at the back and on the outside of the transparent wall.
Figure 30B:
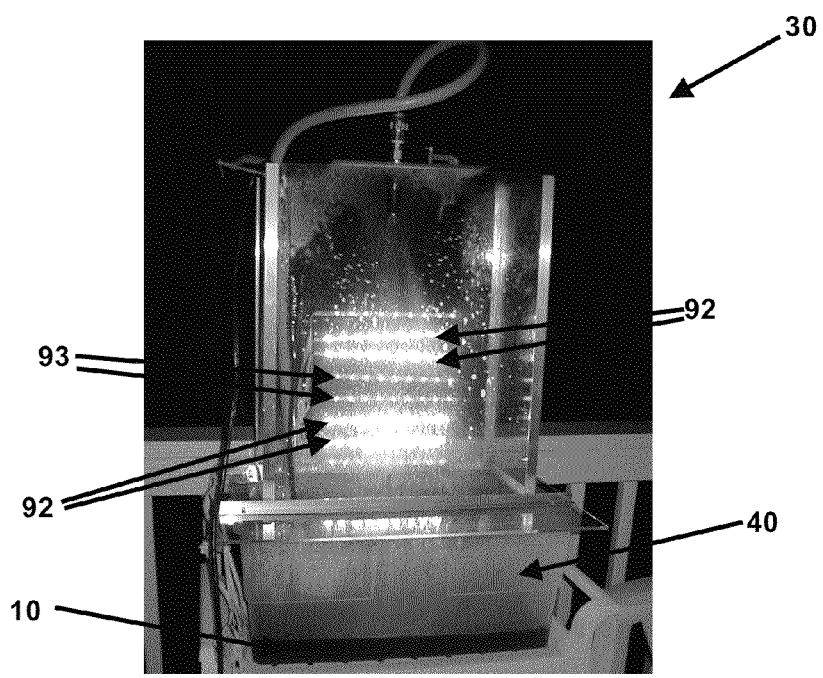

Test Results and Conclusion: FIG. 30A is a photograph of the system used during testing with white and blue light strings located at the back and on the outside of the transparent wall and FIG. 30B is a photograph of the system used during testing with white and red light strings located at the back and on the outside of the transparent wall. The test started at 9:15 pm on Aug. 7, 2009 and was completed at 1:25 am on Aug. 9, 2009. The total spray period was 24 hours and 35 minutes, and consisted of 13 hrs and 22 minutes of sunlight and 11 hrs and 13 min of night operation when the cells were exposed to artificial LED lights only. The test was conducted using a small starter culture of green freshwater algae named *Chlorella*. 7.95 liter (2.1 gallons) of tap water 10 was dropped into a 16 gallon container holding tank 40) and 4 drops of TOPFIN tap water de-chlorinator was added to remove any chlorine. The water was then pumped through the system for 2 minutes before a 250 ml low density starter culture was added.

The light absorbing droplet unit 30 was illuminated at night by eight horizontally positioned 4 W strings of light emitting diodes (LED) with four white light strings 92 providing constant white light the four multicolored light strings 93 provided flashing red, blue, green yellow light in 1 sec intervals.

The pump was stopped at 10:30 am on Aug. 8, 2009 (13 hrs and 15 min after induction) and the light was turned off. One gallon of water had evaporated during the night and was added including a drop of TOPFIN de-chlorinator. Nutrients were included by adding ½ tea spoon of fertilizer containing 20% nitrogen, 20% phosphorus and 20% potassium premixed in ½ cup of water and added to the 2.1 gallon culture. The pump was re-started at 10:40 am and stopped at 8 pm after 9 hrs and 20 min. The system was restarted at 11:25 pm and the light turned on, until the test was permanently stopped at 1:25 am on Aug. 9, 2009 after a total of 24 hrs and 35 min of recirculation and droplet generation. The culture temperature during testing was in the range from 37° C. to 40° C. and peaked at 41.5° C. A separate fan was used to reduce the temperature and keep it below 40° C.

Figure 31:
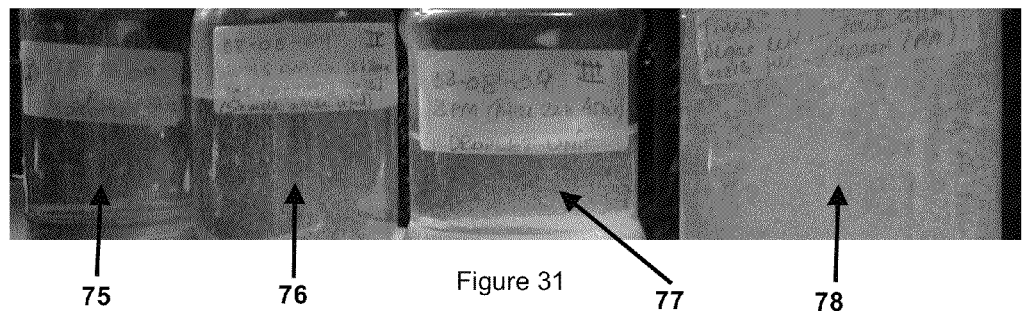
FIG. 31 is a photograph showing cell concentrations after 5 seconds of simultaneous shaking.

Several samples were taken to show increase in cell density. FIG. 31 shows the increase in cell concentration after 5 sec simultaneous shaking of samples marked #I, II, III and IV (from left to right).

Sample I 75, shows cell concentration at the start of testing at 9:15 pm on Aug. 7, 2009 after mixing the starter culture with water. Sample II 76 was taken at 10:45 am on Aug. 8, 2009 just after the pump was re-started at 10:40 am for test run 2. Sample III 77 was taken at 8 pm on Aug. 8, 2009 when pumping was stopped after 9 hr and 20 min. Sample I, II and III was taken directly from the spray nozzle. Sample IV 78 was taken from the bottom of tank after manual stirring at 11:50 am on Aug. 9, 2009.

There was a small increase in cell density in sample II compared with sample I, indicating that some cell splitting had taken place during the night and early morning of August 8th using LED light only. There was a noticeable increase in cell density between sample II and III. Sample IV show a significant increase in density compared to the other samples. None of the samples had dead cells. The conclusions from the successful testing are:

The significant increase in cell density from start to completion of testing, verified the usefulness and capabilities of the system.

A small increase in cell density in sample #II indicated that cell splitting had taken place during the night and early morning of Aug. 8, 2009 after LED light exposure only.

No dead cells were observed in any of the samples after more than 24 hours of recirculation and droplet generation.

Solar Bio Panel: The performance testing with *Chlorella* algae took place on Aug. 7, 2009. The solar bio panel PBR consisted of acrylic sheets and rods. The sheet thickness was ⅛". Square ½" bafflers/rods were used to create flow channels. The unit had the following overall dimensions: Width 40.6 cm×Height: 30.3 cm×Depth 1.9 cm.

Effective light exposed area was 0.206 $m^2$ and the panel's volume was 2 liters with one liter on each side of the sandwich construction. The liquid zigzagged through 6 horizontal channels making the distance from inlet to outlet 2.16 meters. The rectangular channel area in each sandwich section of the panel was 0.00042 $m^2$ making the total area 0.00084 $m^2$ for the panel. Tank volume was 0.00758 $m^3$ (2 gallons)

Figure 32:
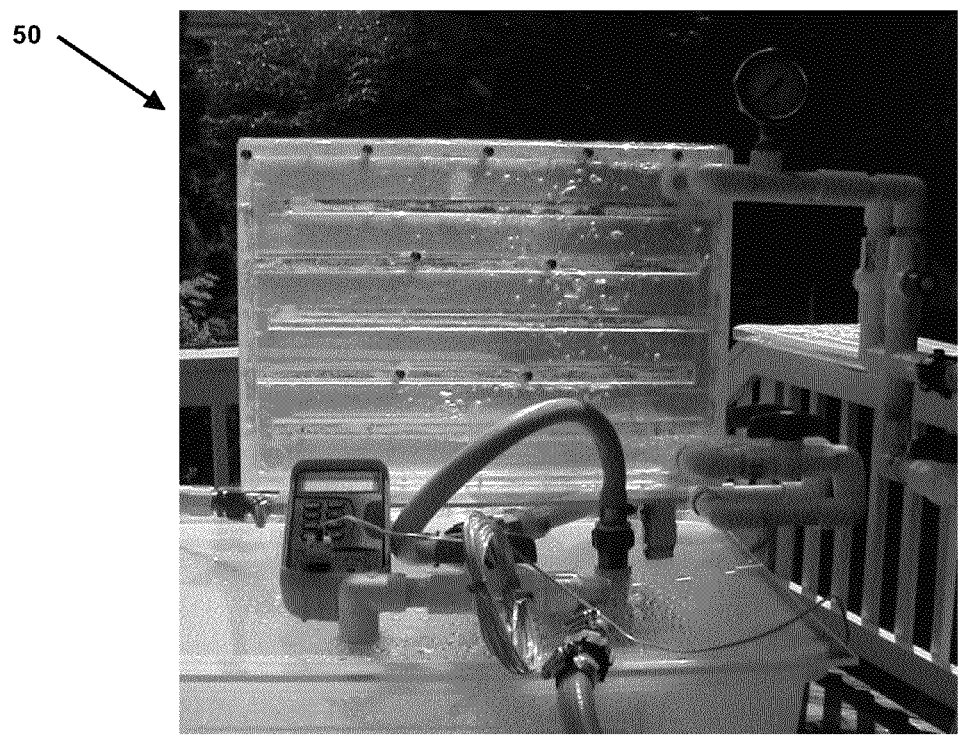
FIG. 32 is a photograph of the solar bio panel during testing with *Chlorella* algae.
Figure 33:
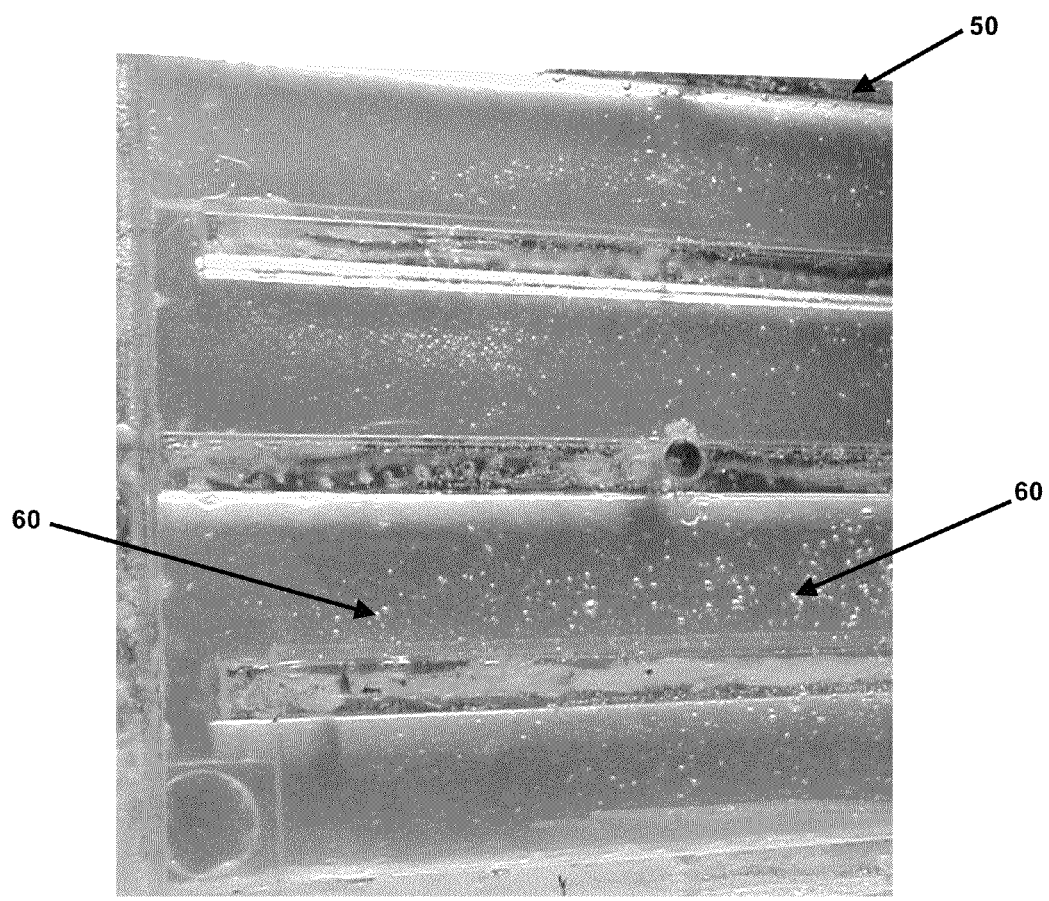
FIG. 33 is a photograph of $CO_2$ enriched air droplets in the solar bio panel.

The purpose of the test was to study (1) hydrodynamic flow patterns in the tank and panel at various capacities, (2) static mixing and level of turbulence in the panel, (3) air bubble distribution of $CO_2$ enriched air and flow of bubbles in the panel, (4) pressure drop through the panel at various capacities and (5) survivability of algae being recirculated in the system. The pump used during testing was a Simer 2305 Geyser II-⅙ HP submersible with name tag capacity of 1260 GPH. The maximum flow through capacity for the test unit was 1.55 m3/h (410 GPH). FIG. 32 show the solar bio panel 50 during testing with *Chlorella* algae on Aug. 7, 2009, and FIG. 33 shows $CO_2$ enriched air droplets 60 in the solar bio panel 50.

Test Results and Conclusions: The fluid velocity in the solar bio panel is a function of pump capacity and the inside area of the flow channel. The duration of light exposure per hour is a function of the panel dimension and is used to calculate exposure per day. The number of cycles per hour is a function of pump capacity and the tank volume. The dynamic surface area is a function of the surface area of the solar panel and the number of cycles per hour or day. Table 2 presents the results from the testing on Aug. 7, 2009 and calculation of data based upon the pump capacity and include the velocity of the cell culture in the solar bio panel, duration in the panel and number of cycles per hour.

TABLE 2

| Capacity (m3/h) | Velocity in panel (m/s) | Duration in panel per cycle (s) | Cycles per hour | Exposure per hour (min) | Exposure per day (hrs) | D-area per hour (m2) | D-area Per day (m2) |
|---|---|---|---|---|---|---|---|
| 0.076 | 0.025 | 86.4 | 10.0 | 14.4 | 5.76 | 2.06 | 49.44 |
| 0.473 | 0.156 | 13.8 | 62.4 | 14.4 | 5.76 | 12.85 | 308.5 |
| 0.726 | 0.24 | 9 | 95.7 | 14.4 | 5.76 | 19.71 | 473.1 |
| 1.000 | 0.33 | 6.6 | 131.9 | 14.5 | 5.76 | 27.17 | 652.1 |
| 1.452 | 0.48 | 4.5 | 192.06 | 14.4 | 5.76 | 39.56 | 949.5 |
| 1.550 | 0.51 | 4.24 | 205.03 | 14.4 | 5.76 | 42.24 | 1,013.7 |

The calculated time for light exposure per day of 5.76 hr represent a combination of sun and artificial light in a 24 hour day of operation. It is worth to notice that a pump capacity of only 1.55 $m^3$/h creates a dynamic surface area equal to 1,014 $m^2$ or about the area of a standard pond.

The hydrodynamic flow pattern in the tank and panel did not change noticeably at increasing capacities. The static mixing device installed inside a flow channel created turbulence and effect forcing cells to rotate to the surface. Injection of $CO_2$ enriched air at the suction side of the pump created various sizes of small micron size bubbles that for the most part floated in the center of the flow channels. The pressure drop through the panel at various capacities was minimal and was recorded at 3.5 psi when the capacity peaked at 410 GPM. The algae survived the pumping and recirculation 4 hour test and no dead cells were observed within two weeks of testing.

During a separate night test with LED light on and off, it was concluded that the LED light located outside of the transparent panels had no measurable increase on the temperature of the culture.

This invention is designed to eliminate technical, chemical and biological limitations known to reduce the effectiveness of current PBR systems. The invention is supposed to increase growth rate, energy efficiency and lower cost of operations compared to current PBRs. The light absorbing droplet unit is providing very simple and ideal conditions for irradiation of microorganisms that greatly minimizes the problem in providing uniform distribution of light to every cell in a high density and deep cell culture. This key advantage coupled with significantly higher culture surface area and $CO_2$ concentration than can be dissolved in water, optimizes the $CO_2$ fixation and the photosynthetic reactions. The two factors are keys for sustained mass production of biofuel from microorganisms. The solar bio panel is needed to provide illumination over a much longer period than the droplet unit does.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

What we claim is:

1. A system for production of microorganisms comprising:
a light absorbing droplet unit, a holding tank, a pump, a flat panel unit and a second pump,
where the light absorbing droplet unit comprises a chamber, a nozzle, and a lighting apparatus, where the chamber comprises four walls, where the walls are transparent, where the nozzle is oriented to spray within the chamber, where the nozzle is fluidly connected to the holding tank, where the lighting apparatus emits light into the chamber through one or more walls of the chamber, where the lighting apparatus comprises a plurality of light emitting diodes, where at least one of the plurality of light emitting diodes emits light at different wavelengths than another of the plurality of light emitting diodes, where the holding tank comprises water, where microorganisms are suspended within the water, where the water comprises diffused carbon dioxide and nutrients, where the water is forced from the holding tank through the nozzle by the pump thereby creating a spray of water within the chamber, where the flat panel unit comprises two flat plates and a plurality of bafflers, where the two flat plates are transparent, where the bafflers are secured between the two flat plates to create channels, where the flat panel unit is fluidly connected to the holding tank, where the second pump forces water from the holding tank through the channels of the flat panel unit.

2. The system of claim 1, where the second pump forces water from the holding tank through the where the flat panel unit is oriented at an incline.

3. The system of claim 1, wherein the light absorbing droplet unit and the flat panel unit are fluidly connected to the holding tank by means of tubing.

4. The system of claim 1, wherein the water flows from the nozzle, through the chamber, back into the holding tank.

5. The system of claim 1, wherein the water flows through the flat panel unit back into the holding tank.

6. The system of claim 1, wherein the plurality of light emitting diodes comprise a red light emitting diode, a white light emitting diode, and a blue light emitting diode.

7. The system of claim 1, wherein the flat panel unit further comprises a lighting apparatus, where the lighting apparatus illuminates the channels of the flat panel unit.

8. The system of claim 1, wherein the water flows through the flat panel unit to the light absorbing droplet unit.

* * * * *